(12) United States Patent
Jung et al.

(10) Patent No.: US 11,452,459 B2
(45) Date of Patent: Sep. 27, 2022

(54) ELECTRONIC DEVICE COMPRISING BIOSENSOR

(71) Applicant: Samsung Electronics Co., Ltd., Suwon-si (KR)

(72) Inventors: Min-Su Jung, Seoul (KR); Yong-Seok Lee, Seoul (KR); Seung-Jae Bae, Yongin-si (KR); Jong-Kyun Im, Yongin-si (KR); Jin-A Mock, Suwon-si (KR); Jin-Young Park, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 380 days.

(21) Appl. No.: 16/486,024

(22) PCT Filed: Nov. 21, 2017

(86) PCT No.: PCT/KR2017/013276
§ 371 (c)(1),
(2) Date: Aug. 14, 2019

(87) PCT Pub. No.: WO2018/151396
PCT Pub. Date: Aug. 23, 2018

(65) Prior Publication Data
US 2020/0046235 A1   Feb. 13, 2020

(30) Foreign Application Priority Data
Feb. 14, 2017   (KR) .................. 10-2017-0019990

(51) Int. Cl.
*A61B 5/024*    (2006.01)
*G06V 40/13*    (2022.01)
(Continued)

(52) U.S. Cl.
CPC .......... *A61B 5/02433* (2013.01); *G06V 40/13* (2022.01); *G06F 21/32* (2013.01); *G06V 40/1341* (2022.01)

(58) Field of Classification Search
CPC .............. A61B 5/02433; A61B 5/6898; A61B 5/02438; A61B 5/02416; A61B 5/318;
(Continued)

(56) References Cited

U.S. PATENT DOCUMENTS

| 2005/0088830 A1 | 4/2005 | Yumoto et al. |
| 2009/0159786 A1 | 6/2009 | Yang et al. |

(Continued)

FOREIGN PATENT DOCUMENTS

| JP | 2005-115337 A | 4/2005 |
| JP | 2013-000157 A | 1/2013 |

(Continued)

*Primary Examiner* — Jonathan A Boyd
(74) *Attorney, Agent, or Firm* — Jefferson IP Law, LLP

(57) ABSTRACT

An electronic device according to an embodiment of the present invention may comprise: a housing comprising a first glass plate, a second glass plate facing in the opposite direction to the first glass plate, and a side member surrounding the space between the first glass plate and the second glass plate, the second plate comprising an outer surface facing in the opposite direction to the first plate and an inner surface facing the first plate; an inner middle plate positioned between the first plate and the second plate; a touch screen display positioned between the middle plate and the first plate; an opaque layer comprising a first opening and a second opening positioned within 150 mm from the first opening, the opaque layer being directly or indirectly attached to the inner surface of the second plate comprising a hole overlapping with the first opening but comprising no hole overlapping with the second opening; a camera assembly partially positioned inside the hole of the second plate and the first opening; a light-emitting diode (LED) posi- (Continued)

tioned between first parts of the second opening while facing the second opening and functionally connected to the camera assembly; a heart rate monitor (HRM) assembly positioned between second parts of the second opening while facing the second opening, the second opening having a gap between the heart rate monitor (HRM) assembly and the inner surface of the second plate, and the heart rate monitor (HRM) assembly comprising a light-discharging element and a light-receiving element; and a light guide structure comprising a first part between the LED and the second plate and a second part between the heart rate monitor (HRM) assembly and the second plate, the light guide structure being configured such that, when seen from above the second plate, the first part surrounds the LED, while the second part surrounds the light-discharging element.

15 Claims, 19 Drawing Sheets

(51) Int. Cl.
*G06F 21/32* (2013.01)
*G06V 40/12* (2022.01)

(58) Field of Classification Search
CPC ....... G06K 9/00013; G06K 2009/0006; G06K 9/0004; G06F 21/32; G06F 1/16; G06F 3/041; G06F 1/1684; G06F 1/1686
See application file for complete search history.

(56) References Cited

U.S. PATENT DOCUMENTS

| | | |
|---|---|---|
| 2011/0065482 A1 | 3/2011 | Koide et al. |
| 2012/0258773 A1 | 10/2012 | Rivera et al. |
| 2015/0190094 A1* | 7/2015 | Lee ................... A61B 5/02427 600/479 |
| 2016/0033342 A1 | 2/2016 | Lyon et al. |
| 2016/0188950 A1 | 6/2016 | Liu et al. |
| 2016/0246396 A1* | 8/2016 | Dickinson ........... G06F 3/03545 |
| 2016/0275334 A1 | 9/2016 | Hama et al. |

FOREIGN PATENT DOCUMENTS

| | | |
|---|---|---|
| JP | 2013-257609 A | 12/2013 |
| KR | 10-2009-0067075 A | 6/2009 |
| KR | 10-2015-0071364 A | 6/2015 |
| KR | 10-2015-0082029 A | 7/2015 |

* cited by examiner

ELECTRONIC DEVICE COMPRISING BIOSENSOR

CROSS-REFERENCE TO RELATED APPLICATION(S)

This application is a U.S. National Stage application under 35 U.S.C. § 371 of an International application number PCT/KR2017/013276, filed on Nov. 21, 2017, which is based on and claimed priority of a Korean patent application number 10-2017-0019990, filed on Feb. 14, 2017, in the Korean Intellectual Property Office, the disclosure of which is incorporated by reference herein in its entirety.

TECHNICAL FIELD

An embodiment of the disclosure relates to an electronic device that provides a biosensor.

BACKGROUND ART

Recently, electronic devices such as portable terminals with novel functions have developed rapidly, and as the distribution of the portable terminals has expanded, the number of people utilizing electronic devices such as portable terminals has also increased.

Typically, display devices used in the portable terminals are for outputting an image or image information, and electronic devices provide information and communication interfaces through the display. Thanks to the development of electric and electronic technologies, display device performance has developed, and thus display device image quality has improved. Such display devices, which have been integrated with touch panels or the like, have been utilized not only as output devices, but also as input devices.

In accordance with the development of technology and the demand of consumers who enjoy images on electronic devices, large-area displays are being developed in earnest. The displays are provided therein with sensors or the like that are capable of recognizing and identifying a user through a connection with a part of the user's body, as well as calculating horizontal elements of an input (e.g., a position or a movement) on the basis the input to the touch panel.

DETAILED DESCRIPTION OF THE INVENTION

Technical Problem

An electronic device may include a display driver module (a display driver IC), a front camera, and illuminance and proximity sensors disposed in the upper bezel area thereof, and may also include a function key module and a biosensor based on various types of touch inputs disposed in the lower bezel area thereof. Accordingly, because the display driver module or the like disposed inside the bezel area occupies a large volume it may be difficult to implement a large-area display extended in the longitudinal direction.

In addition, since a fingerprint recognition sensor has a hardware structure separate from the display, a separate space may be required, and the position and space of the fingerprint recognition sensor may be restricted as mobile devices become smaller and slimmer.

Various embodiments of the disclosure provide an electronic device for implementing a large-area display.

Technical Solution

According to an embodiment of the disclosure, an electronic device may include: a housing including a first glass plate, a second glass plate facing away from the first glass plate, and a side member surrounding a space between the first glass plate and the second glass plate, the second plate including an outer face facing away from the first plate and an inner face facing the first plate; an inner intermediate plate located between the first plate and the second plate; a touch screen display located between the intermediate plate and the first plate; an opaque layer including a first opening and a second opening located within a distance of 150 mm from the first opening, the opaque layer directly or indirectly attached to the inner face of the second plate that includes a hole overlapping the first opening but does not include a hole overlapping the second opening; a camera assembly having a portion positioned in the hole of the second plate and the first opening; a Light-Emitting Diode (LED) positioned between first portions of the second opening while facing the second opening, and functionally connected to the camera assembly; a Heart Rate Monitor (HRM) assembly positioned between second portions of the second opening while facing the second opening, the second opening having a gap between the HRM assembly and an inner face of the second plate, and the HRB assembly including a light-emitting element and a light-receiving element; and a light guide structure including a first portion between the LED and the second plate and a second portion between the HRM assembly and the second plate, the first portion surrounding the LED and the second portion surrounding the light-emitting element when viewed from above the second plate.

According to an embodiment of the disclosure, an electronic device may include: a housing including a display device including a first glass plate exposed to be oriented in a first direction and a second glass plate face oriented in a second direction to face away from the first glass plate, the housing further including a transparent area that forms at least a portion of the second plate; a printed circuit unit disposed inside the housing; an illumination unit disposed between the transparent area and the printed circuit board and electrically connected to the printed circuit board, the illumination unit being configured to emit light towards the transparent area; and a biosensor disposed between the transparent area and the printed circuit board and electrically connected to at least a portion of the printed circuit board so as to sense light transmitted through the transparent area.

Advantageous Effects

An electronic device according to various embodiments of the disclosure makes it possible to simplify the structure and to reduce a manufacturing cost by integrating a biosensor and an illumination unit on a rear cover.

An electronic device according to various embodiments of the disclosure is configured such that the area in which the biosensor and the illumination unit disposed on the rear cover is seamlessly connected to other areas of the rear cover without being disconnected, which makes it possible to provide a beautiful design as a whole.

MODE FOR CARRYING OUT THE INVENTION

Figure 1:
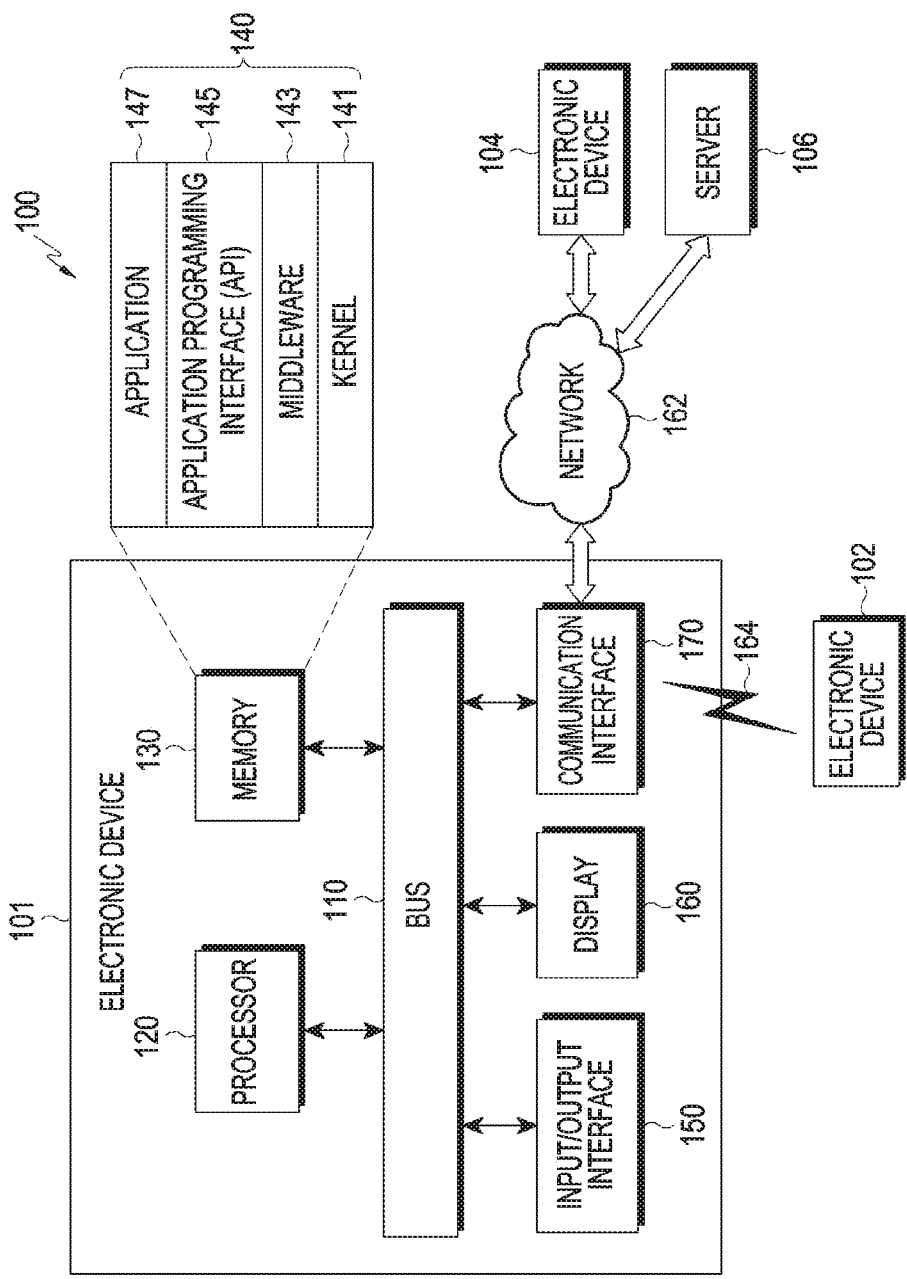
FIG. 1 is a schematic view illustrating an electronic device according to one of various embodiments within a network environment.

Hereinafter, various embodiments of the disclosure will be described with reference to the accompanying drawings. The embodiments and the terms used therein are not intended to limit the technology disclosed herein to specific forms, and should be understood to include various modifications, equivalents, and/or alternatives to the corresponding embodiments. In describing the drawings, similar reference numerals may be used to designate similar elements. A singular expression may include a plural expression unless the context clearly indicates otherwise. In the disclosure, the expression "A or B" or "at least one of A and/or B" may include all possible combinations of items enumerated together. The expression "a first", "a second", "the first", or "the second" may modify corresponding elements regardless of the order or the importance thereof, and are used merely to distinguish each element from the others without unduly limiting the elements. When an element (e.g., first element) is referred to as being "(functionally or communicatively) connected", or "coupled" to another element (second element), the element may be connected directly to said another element or connected to the another element through yet another element (e.g., third element).

In the disclosure, the expression "configured to" may be used interchangeably with, for example, "suitable for", "having the capacity to", "adapted to", "made to", "capable of", or "designed to" in terms of hardware or software, according to circumstances. In some situations, the expression "device configured to" may mean that the device, together with other devices or components, "is able to". For example, the phrase "processor adapted (or configured) to perform A, B, and C" may mean a dedicated processor (e.g., embedded processor) only for performing the corresponding operations or a general-purpose processor (e.g., Central Processing Unit (CPU) or Application Processor (AP)) that can perform the corresponding operations by executing one or more software programs stored in a memory device.

An electronic device according to various embodiments of the disclosure may include at least one of, for example, a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), an MPEG-1 audio layer-3 (MP3) player, a medical device, a camera, and a wearable device. The wearable device may include at least one of an accessory type (e.g., a watch, a ring, a bracelet, an anklet, a necklace, glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit). In some embodiments, the electronic device may include at least one of, for example, a television, a Digital Video Disk (DVD) player, an audio player, a refrigerator, an air conditioner, a vacuum cleaner, an oven, a microwave oven, a washing machine, an air cleaner, a set-top box, a home automation control panel, a security control panel, a media box (e.g., Samsung HomeSync™, Apple TV™, or Google TV™), a game console (e.g., Xbox™ and PlayStation™), an electronic dictionary, an electronic key, a camcorder, and an electronic photo frame.

In other embodiments, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, a scanning machine, and an ultrasonic machine), a navigation device, a Global Navigation Satellite System (GNSS), an Event Data Recorder (EDR), a Flight Data Recorder (FDR), a Vehicle Infotainment Device, electronic devices for a ship (e.g., a navigation device for a ship, a gyro-compass, etc.), avionics, a security device, an automotive head unit, a robot for home or industry, a drone, an Automatic Teller Machine (ATM) in banks, a Point Of Sale (POS) device in a shop, and Internet-of-things devices (e.g., a light bulb, various sensors, a sprinkler device, a fire alarm, a thermostat, a streetlamp, a toaster, athletic equipment, a hot water tank, a heater, a boiler, etc.). According to some embodiments, an electronic device may include at least one of furniture, a part of a building/structure or car, an electronic board, an electronic signature receiving device, a projector, and various types of measuring instruments (e.g., a water meter, an electric meter, a gas meter, a radio wave meter, etc.). In various embodiments, the electronic device may be flexible, or may be a combination of two or more of the above-described various devices. The electronic device according to embodiments of the disclosure is not limited to the above-described devices. In the disclosure, the term "user" may indicate a person who uses an electronic device or a device (e.g., an artificial intelligence electronic device) using an electronic device.

An electronic device 101 within a network environment 100 according to various embodiments will be described with reference to FIG. 1. The electronic device 101 may include a bus 110, a processor 120, a memory 130, an input/output interface 150, a display 160, and a communication interface 170. In some embodiments, at least one of the elements of the electronic device 100 may be omitted therefrom, or the electronic device 100 may further include other elements. The bus 110 may include a circuit configured to interconnect the elements 110 to 170 and deliver communication (e.g., a control message or data) between the elements. The processor 120 may include one or more of a Central Processing Unit (CPU), an Application Processor (AP), and a Communication Processor (CP). The processor 120, for example, may be configured to execute operations or data processing related to the control and/or communication of at least one other element of the electronic device 101.

The memory 130 may include a volatile and/or non-volatile memory. The memory 130 may be configured to store, for example, instructions or data related to at least one other element of the electronic device 101. According to an embodiment, the memory 130 may store software and/or a program 140. The program 140 may include, for example, a kernel 141, middleware 143, an Application Programming Interface (API) 145, and/or application programs (or "applications") 147. At least some of the kernel 141, the middleware 143, and the API 145 may be referred to as an "Operating System (OS)". The kernel 141 may control or manage, for example, system resources (e.g., the bus 110, the processor 120, and the memory 130) used to execute operations or functions implemented by other programs (e.g., the middleware 143, the API 145, and the application programs 147). Also, the kernel 141 may provide an interface through which the middleware 143, the API 145, or the application programs 147 may access the individual elements of the electronic device 101 so as to control or manage the system resources.

The middleware 143 may serve as, for example, an intermediary that enables the API 145 or the application programs 147 to communicate with the kernel 141 to exchange data. Also, the middleware 143 may process one or more task requests received from the application programs 147 according to the priorities of the task requests. For example, the middleware 143 may assign priorities which allow use of the system resources (e.g., the bus 110, the processor 120, the memory 130, etc.) of the electronic device 101 to one or more of the application programs 147, and may process the one or more task requests. The API 145 is an interface through which the applications 147 control functions provided by the kernel 141 or the middleware 143, and may include, for example, at least one interface or function (e.g., instruction) for file control, window control, image processing, text control, and the like. The input/output interface 150, for example, may be configured to deliver, to the other element(s) of the electronic device 101, commands or data input from a user or a different external device. Alternatively, the input/output interface 150 may be configured to output, to the user or the different external device, commands or data received from the other element(s) of the electronic device 101.

Examples of the display 160 may include a Liquid Crystal Display (LCD), a Light-Emitting Diode (LED) display, an Organic Light-Emitting Diode (OLED) display, a MicroElectroMechanical Systems (MEMS) display, and an electronic paper display, or the like. The display 160 may display, for example, various types of content (e.g., text, images, videos, icons, symbols, etc.) to a user. The display 160 may include a touch screen, and may receive, for example, a touch, gesture, proximity, or hovering input using an electronic pen or a part of a user's body. The communication interface 170 may be configured to establish, for example, communication between the electronic device 101 and an external device (e.g., a first external electronic device 102, a second external electronic device 104, or a server 106). For example, the communication interface 170 may be configured to be connected to a network 162 through wireless communication or wired communication so as to communicate with the external device (e.g., the second external electronic device 104 or the server 106).

The wireless communication may use, for example, at least one of Long-Term Evolution (LTE), LTE-Advance (LTE-A), Code Division Multiple Access (CDMA), Wideband CDMA (WCDMA), Universal Mobile Telecommunications System (UMTS), Wireless Broadband (WiBro), Global System for Mobile communications (GSM), and the like, as a cellular communication protocol. According to an embodiment, the wireless communication may include, for example, at least one of Wi-Fi, Bluetooth, Bluetooth Low Energy (BLE), Zigbee, Near Field Communication (NFC), magnetic secure transmission, Radio Frequency (RF), and Body Area Network (BAN). According to an embodiment, the wireless communication may include Global Navigation Satellite System (GNSS). The GNSS may include, for example, at least one of a Global Positioning System (GPS), a Global Navigation Satellite System (Glonass), a Beidou Navigation Satellite System (hereinafter, "Beidou"), and a European Global Satellite-based Navigation System (Galileo). Hereinafter, the "GPS" may be interchangeably used herein with the "GNSS". The wired communication may include, for example, at least one of a Universal Serial Bus (USB), a High Definition Multimedia Interface (HDMI), Recommended Standard 232 (RS-232), power line communication, a Plain Old Telephone Service (POTS), and the like. The network 162 may include at least one of a telecommunication network such as a computer network (e.g., a LAN or a WAN), the Internet, and a telephone network.

Each of the first and second external electronic devices 102 and 104 may be of a type identical to, or different from, that of the electronic device 101. According to various embodiments, all or some of the operations executed in the electronic device 101 may be executed in another electronic device or multiple electronic devices (e.g., the electronic devices 102 and 104 or the server 106). According to an embodiment, when the electronic device 101 has to perform some functions or services automatically or in response to a request, the electronic device 101 may request another device (e.g., the electronic device 102 or 104 or the server 106) to execute at least some functions relating thereto, instead of, or in addition to, executing the functions or services by itself. Said another electronic device (e.g., the electronic device 102 or 104 or the server 106) may execute the requested functions or the additional functions and may deliver an execution result to the electronic device 101. The electronic device 101 may process the received result as it is or additionally so as to provide the requested functions or services. To this end, cloud computing, distributed computing, or client-server computing technology may be used.

Figure 2A:
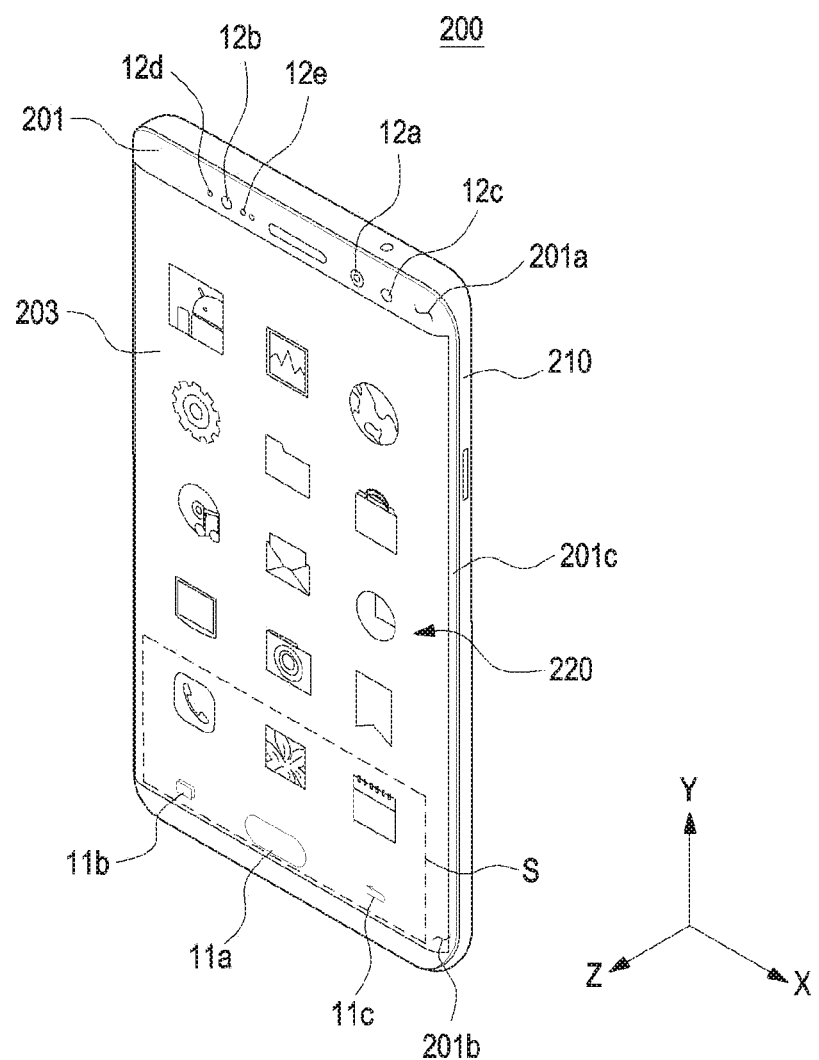
FIG. 2A is a perspective view illustrating an electronic device according to one of various embodiments of the disclosure.
Figure 2B:
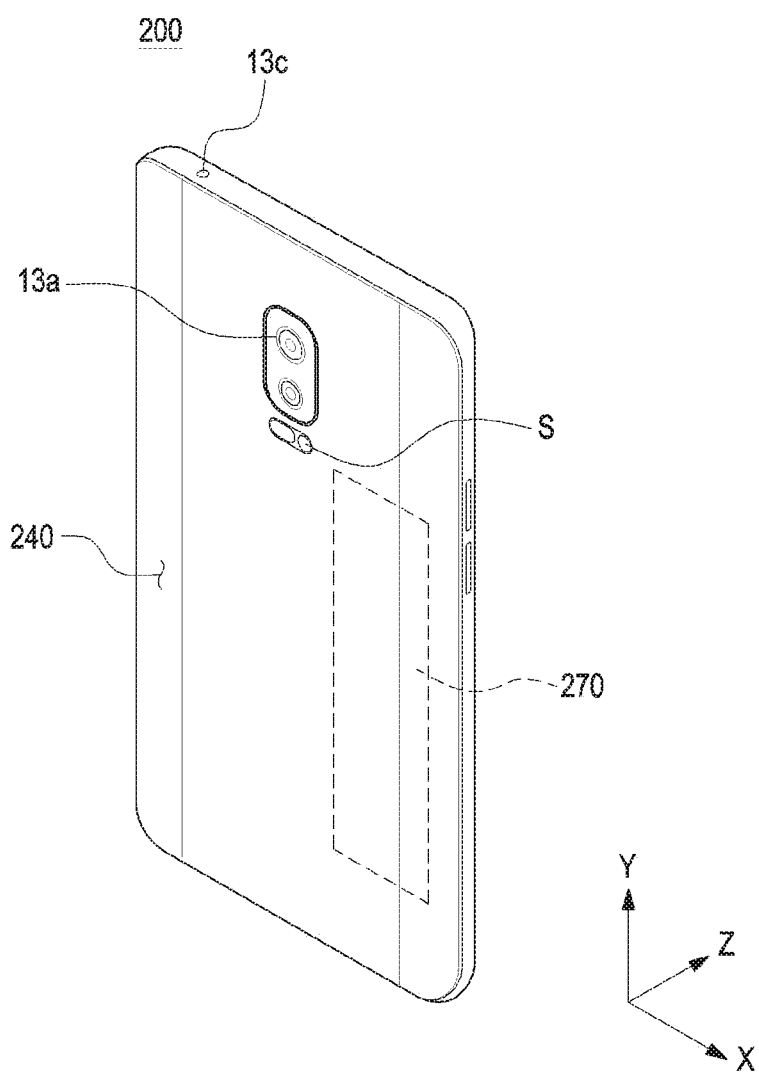
FIG. 2B is a perspective view illustrating the electronic device according to one of various embodiments of the disclosure, in which the electronic device is viewed in another direction.

FIG. 2A is a perspective view illustrating an electronic device 200 according to one of various embodiments of the disclosure. FIG. 2B is a perspective view illustrating the electronic device 200 according to one of various embodiments of the disclosure, which is viewed in another direction.

In FIGS. 2A and 2B, the "X axis" in an orthogonal coordinate system of three axes may correspond to the width direction of the electronic device 200, the "Y axis" may correspond to the length direction of the electronic device 200, and the "Z axis" may correspond to the thickness direction of the electronic device 200. In addition, in an embodiment of the disclosure, the "X-axis direction" may mean a first direction (+X, −X), the "Y-axis direction" may mean a second direction (+Y, −Y), and the "Z-axis direction" may mean a third direction (+Z, −Z).

As illustrated in FIGS. 2A and 2B, the electronic device 200 may include a housing 210 and a display device 220. The front face of the housing 210 may open, and a first glass plate 203 may be mounted to form at least a portion of the front face 201 of the housing 210 so as to close the open front face 210 of the housing 210. The electronic device 200 may be provided with a keypad, for example, on the front face of the housing 210. The key pad includes touch keys 11a, 11b, and 11c, which are provided at one side area of the first glass plate 203 and are capable of generating input signals by being touched by the user's body.

According to various embodiments, the housing 210 is configured to accommodate various electronic components and the like, and at least a portion of the housing 110 may be made of a conductive material. For example, the housing 210 may include side walls that form the outer faces of the electronic device 200, and the externally exposed portions of the electronic device 200 may be made of a conductive metal material. A printed circuit board (not illustrated) and/or a battery 270 may be accommodated in the housing 210. For example, a processor, a communication module, various interfaces (e.g., interfaces 150 and 170 in FIG. 1), a power management module, and the like may be mounted on the printed circuit unit (not illustrated) in the form of integrated circuit chips. As another example, a control circuit may also be configured as an integrated circuit chip and may be mounted on the printed circuit board. For example, the control circuit may be a portion of the above-described processor or communication module. Power can be secured by housing the battery 270 in the housing 210.

According to various embodiments of the disclosure, a first camera 12a, an illuminance sensor 12b, or a proximity sensor 12c may be arranged in the upper end area of the front face of the electronic device 200. In still another example, a second camera 13a, a flash, or a speaker 13c may be arranged on the rear face of the electronic device 200.

According to various embodiments, the display device 220 may be exposed through the front face of the housing 210. At least a portion of the display device 220 may be made of a material that transmits radio waves or magnetic fields, and may be mounted on the front face of the housing 210. The display device 220 may include a display panel mounted on an inner face of a first glass plate 203, which is made of a tempered glass material. A touch panel may be mounted between the first glass plate 203 and the display panel. For example, the display device 220 may be an output device for outputting a screen, and may be utilized as an input device provided with a touch screen function.

According to various embodiments, the electronic device 200 may include a second glass plate 240 that protects the rear face of the housing 210. The second glass plate 240 may be installed to be oriented in a direction that is opposite the display device 220, and may be made of a material capable of transmitting radio waves or magnetic fields (e.g., tempered glass or synthetic resin). The second glass plate 240 may form the external appearance of the electronic device 200 together with the housing 210 and the display device 220.

According to various embodiments of the disclosure, the electronic device 200 may have a biometric sensing area S for recognizing biometric information in at least a portion of an active area of the display (an area in which actual display pixels are implemented so as to display information). Since the biometric sensing area S is formed in the active area of the front face of the electronic device 200 or disposed on the second glass plate 240, it is possible to utilize most of the front face of the electronic device 200 as the display.

Hereinafter, a structure for extending most of the front face of the electronic device as the display will be described.

Figure 3:
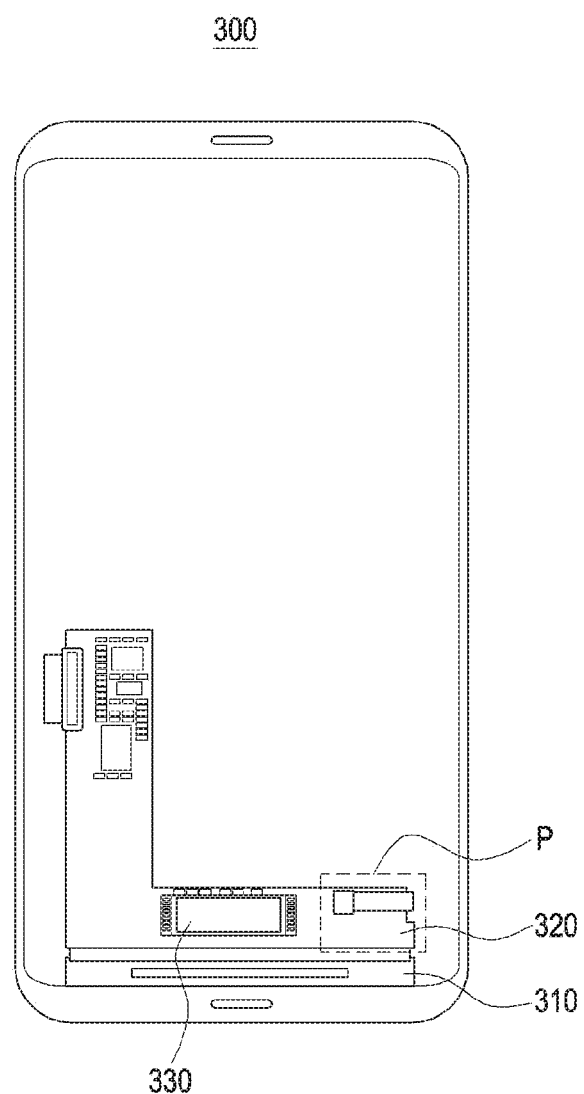
FIG. 3 is a front view illustrating the front inner structure of an electronic device 300 according to various embodiments of the disclosure.
Figure 4:
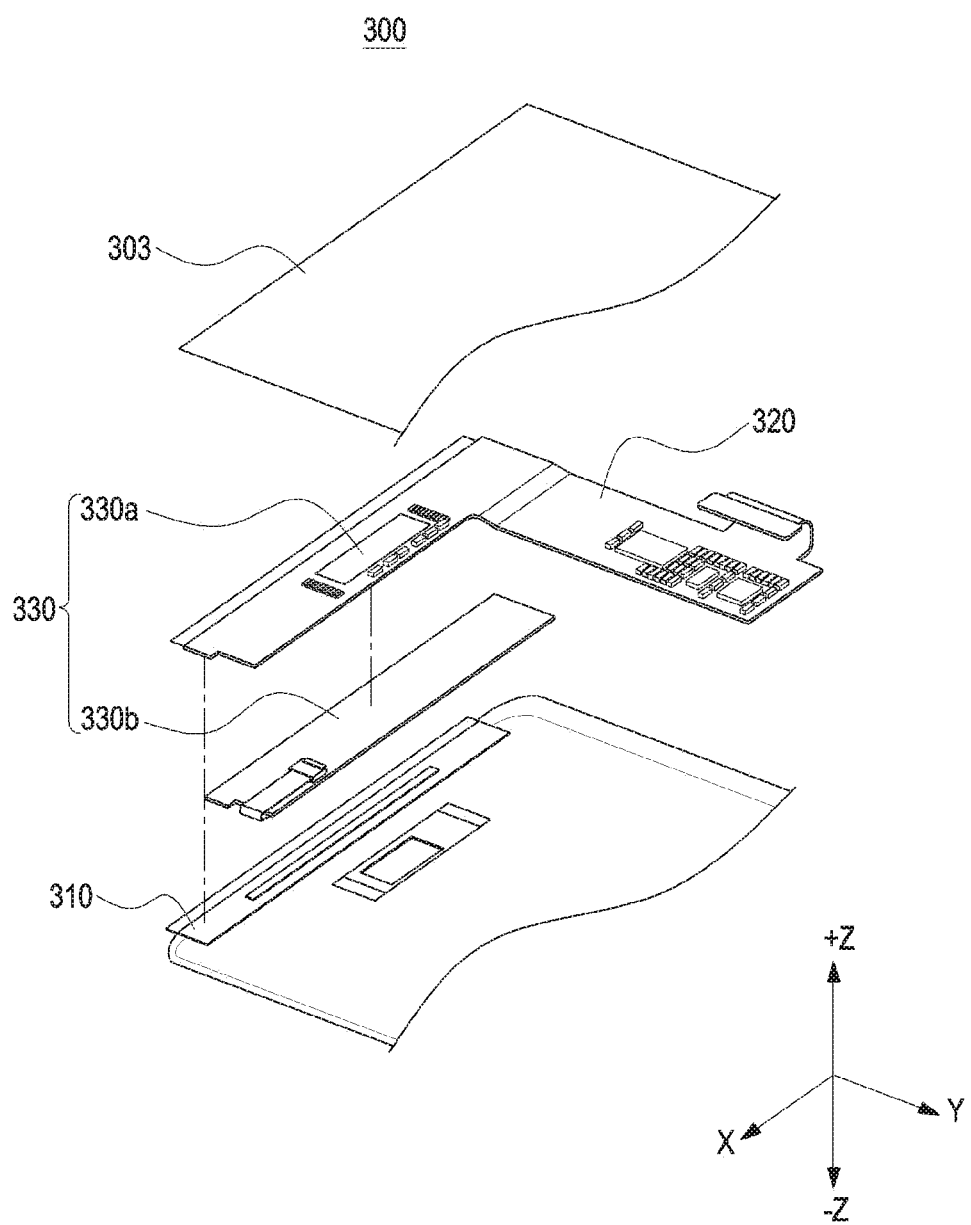
FIG. 4 is an exploded perspective view illustrating the front inner structure of the electronic device 300 according to various embodiments of the disclosure.

FIG. 3 is a front view illustrating the front inner structure of an electronic device 300 according to various embodiments of the disclosure. FIG. 4 is an exploded perspective view illustrating the front inner structure of the electronic device 300 according to various embodiments of the disclosure.

According to various embodiments of the disclosure, in order to implement a large-area display device (the display device 220 in FIG. 2A) on the front face of the electronic device 300, a certain structure and an arrangement relationship may be required between the components arranged in the front area and rear area of the electronic device. According to an embodiment, a display printed circuit board (PCB) 320 including a display driver IC (DDI) and biosensors (e.g., a pressure sensor and/or a fingerprint sensor) may be disposed in the lower end of the front area of the electronic device 300.

Referring to FIGS. 3 and 4, the electronic device 300 may include a display panel 303 (the display device 220 in FIG. 2A), a display driver module 310 (e.g., a display driver IC (DDI)), a display PCB 320, or at least one sensor 330. The structure of the display driver module 310 (e.g., the display driver IC (DDI)), the display PCB 320, or the at least one sensor 330 of the electronic device 300 illustrated in FIGS. 3 and 4 may be partially or wholly the same as the structure of the display 160, the processor 120, or the input/output interface 150 of FIG. 1.

According to various embodiments, the display driver module 310 may be disposed in the lower end area of the electronic device 300. The display driver module 310 (e.g., a display driver IC (DDI)) may control the display panel 303 including multiple pixels and at least some of the multiple pixels included in the display panel 303 so as to provide display information. The display driver module may act as a barrier to the expansion of the upper end area of the display because it occupies a large volume with a front camera (the first camera 12a in FIG. 2A) in the upper end area of the electronic device. According to an embodiment of the disclosure, by changing the arrangement position of the display driver module 310 to the lower end area of the electronic device 300, the upper end bezel area of the electronic device 300 may be reduced and the display may be extended in the longitudinal direction.

According to various embodiments, the display driver module 310 may be arranged to be electrically connected to the display PCB 320, and the display driver module 310 may be disposed such that a portion thereof overlaps the lower end bezel area or the extended display.

According to various embodiments, the display PCB 320 may be disposed in the rear area of the display panel 303. Electronic components for driving the display may be mounted on the display PCB 320, which may be electrically connected to the display. For example, the display PCB 320 may include a flexible printed circuit board (FPCB). One end of the display PCB 320 may be connected to and extend from the display panel 303, and the at least one sensor 330 may be disposed on the other end of the display PCB 320. The at least one sensor 330 disposed on the other end may be disposed on one face of the display PCB 320, which is oriented in a first direction (+Z) or in a second direction (−Z) opposite the first direction (+Z).

According to various embodiments, a portion of the display PCB 320 may be bent such that the area except for the portion connected to the display panel 303 is arranged to face one face of the display panel 303. At least one sensor 330b may be disposed in the area such that the display panel 303 and the at least one sensor 330 may overlap each other when viewed from the front side of the electronic device. The at least one sensor 330 may include a force sensor 330b, and the pressure sensor disposed in the area may contribute to the extension in the longitudinal direction since it does not occupy a separate space in the upper end portion and/or the lower end portion of the display.

According to various embodiments, the at least one sensor 330 may include a fingerprint sensor 330a, and the fingerprint sensor 330a may be disposed on a face where the face on which the pressure sensor 330b with reference to the display PCB 320.

According to various embodiments, apart being disposed on the front face of the electronic device 300 to be oriented in the first direction (+Z), the biosensor 330 such as the fingerprint sensor disposed on the display PCB 320 according to various embodiments of the disclosure may be disposed on the rear face of the electronic device 300 to be oriented in the second direction (−Z) so as to reduce the restriction of the mounting space, thereby contributing to the manufacture of a large-area display.

Figure 5:
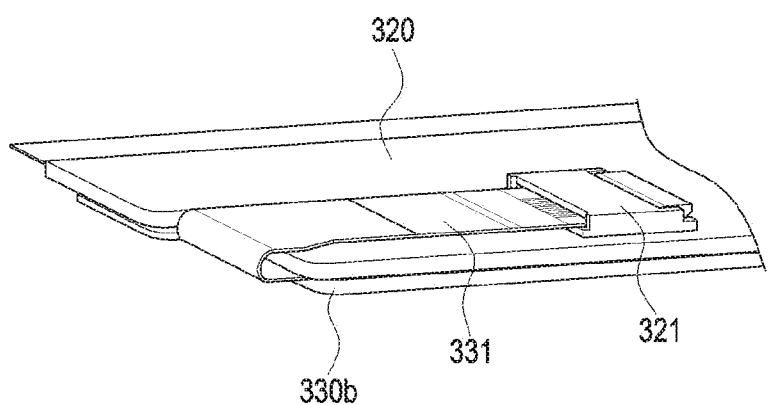
FIG. 5 is a perspective view illustrating an electrical connection configuration of a display printed circuit board 320 and at least one sensor 330b in an electronic device according to various embodiments of the disclosure.

FIG. 5 is a perspective view illustrating an end face of an electrical connection configuration of a display PCB 320 and at least one sensor 330 according to various embodiments of the disclosure, which corresponds to the area P in FIG. 3. The structure of the display PCB 320 or the at least one sensor 330b of the electronic device 300 illustrated in FIG. 5 may be partially or wholly the same as that of the display PCB 320 or the at least one sensor 330 of the electronic device 300 illustrated in FIGS. 3 and 4.

Referring to FIG. 5, the electronic device may include a display PCB 320 or at least one sensor 330b.

According to various embodiments, the electrical connection between the display PCB 320 and the at least one sensor 330b (e.g., a pressure sensor) may be formed in such a manner in which a connection portion 331 extending from the pressure sensor 330b is bent and is electrically connected to a connector 321 of the display PCB 320.

According to various embodiments, an adhesive member (e.g., tape) is disposed on each side of the display PCB 320, and one face of the pressure sensor 330b may be entirely attached to the display PCB 320 via the adhesive member, whereby the pressure sensor 330b and display PCB 320 may be integrally implemented.

Figure 6:
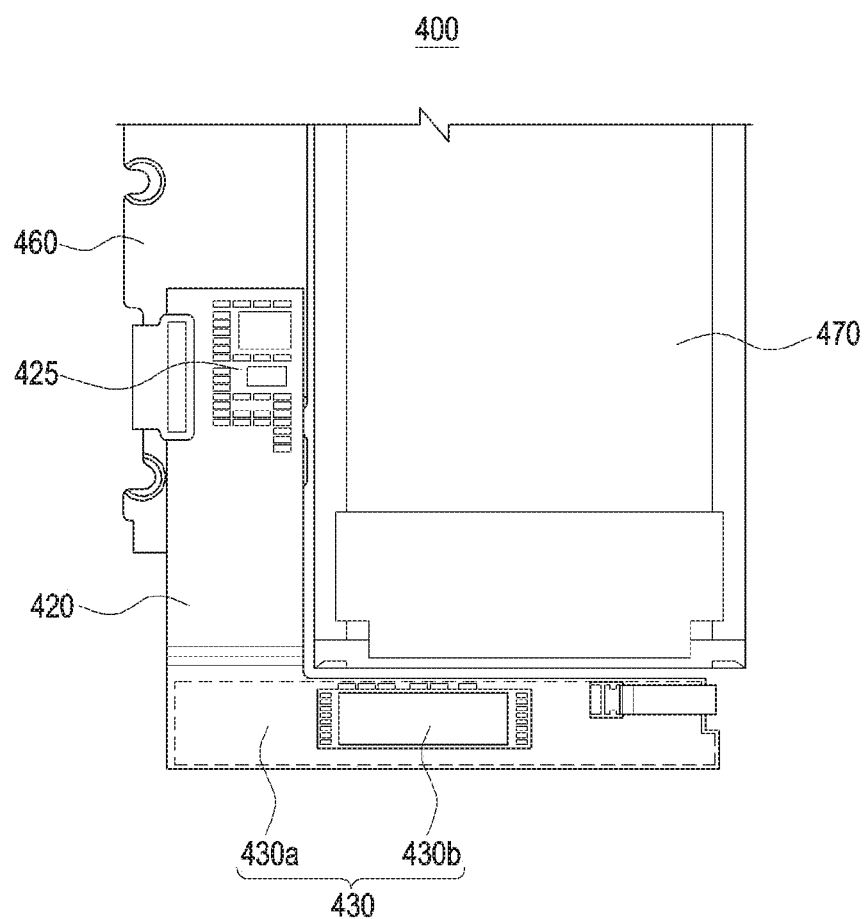
FIG. 6 is a projection view illustrating a structure in which a display device drive component 425 is mounted in an area in which a main printed circuit board 460 of an electronic device 400 according to various embodiments of the disclosure is disposed.

FIG. 6 is a projection view illustrating a structure in which a display device drive component 425 is mounted in an area in which a main printed circuit board 460 of an electronic device 400 according to various embodiments of the disclosure is disposed. The structure of the display PCB 420 or the at least one sensor 430 of the electronic device 400 illustrated in FIG. 6 may be partially or wholly the same as that of the display PCB 320 or the at least one sensor 330 of the electronic device 300 illustrated in FIGS. 3 and 4.

Referring to FIG. 6, the electronic device 400 may include a battery 470 disposed inside the electronic device, a main PCB 460 disposed in a peripheral area of the battery 470, and a display PCB 420 connected to the main PCB 460.

According to various embodiments, the battery 470 may be disposed on the rear face of the display device (the display device 220 of FIG. 2A), and the display PCB 420 is disposed on a portion of a side face and the lower end area of the battery 470. For example, when viewed from the rear side of the electronic device 400, the display PCB 420 may have an "L" shape. The main PCB 460 may be disposed on another portion of the side face of the battery 470, and may be electrically connected to a portion of a side face of the display PCB 420. The lower end area of the display PCB 420 is a portion on which the at least one sensor 430 described above is disposed, and the sensor 430 may be electrically connected to at least a portion of the display PCB 420.

According to various embodiments, as the display PCB 420 extends to a side face area of the battery 470, an area of the display PCB 420 may overlap a portion of the main PCB 460. A display device drive component 425 may be disposed in the overlapping area, and thus the problem of insufficient mounting area of the display PCB 420 may be solved.

In the case in which the display device drive component is disposed on the display PCB 420, which is disposed only in the lower end area of the battery 470, the mounting space in the longitudinal direction of the battery 470 may be restricted, which may result in capacitance reduction of the battery. Thus, according to an embodiment of the disclosure, by extending the display PCB 420 to the side area (e.g., an area disposed on the main PCB 460), which is irrespective of the longitudinal arrangement of the battery 470, and by mounting the display device drive component 425 on the overlapping area, it is possible to reduce the influence on the size of the battery 470.

Hereinafter, the structures and arrangement relationships of components (e.g., biosensors) disposed in an area of the rear face of the electronic device in order to implement a large-area display will be described.

Figure 7:
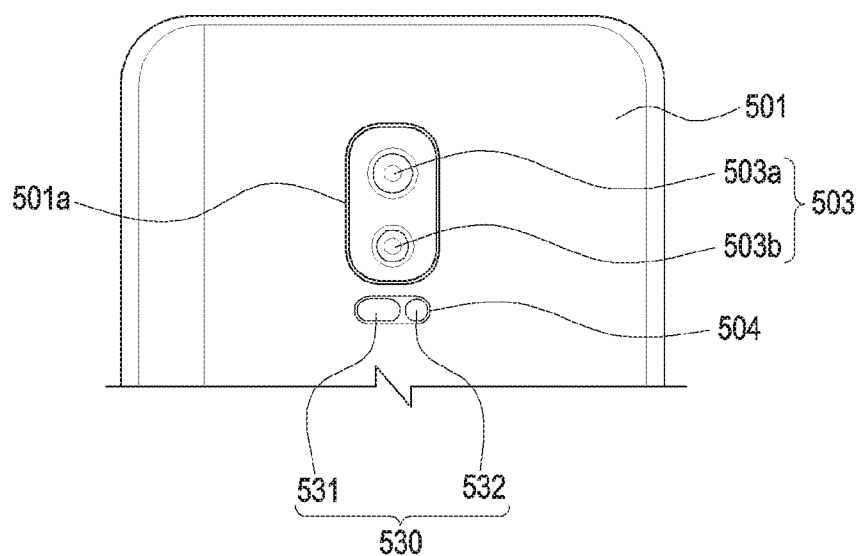
FIG. 7 is a front view illustrating a portion of a second plate of the electronic device according to various embodiments of the disclosure illustrated in FIG. 2B.

FIG. 7 is a front view illustrating a portion of the second plate of the electronic device according to various embodiments of the disclosure illustrated in FIG. 2B.

According to various embodiments of the disclosure, in order to implement a large-area display device (the display device 220 in FIG. 2A) on the front face of the electronic device 500, a certain structure and an arrangement relationship may be required between the components arranged in the front area and rear area of the electronic device. According to an embodiment, a biometric sensing unit 530 including a biosensor may be implemented in an area of the second plate 501 corresponding to the rear cover of the electronic device 500.

Referring to FIG. 7, the electronic device 500 may include a second plate 501 having a face oriented in the second direction (the second direction (−Z) in FIG. 2B), a camera assembly 503 disposed on the second plate 501, a biosensor 531, an illumination unit 532, and the like. The structure of the biometric sensing unit 530 including the second plate 501, the camera assembly 503, and the biosensor of the electronic device 500 illustrated in FIG. 7 may be partially or wholly the same as the structure of the second glass plate 240 and the camera 13a of the electronic device 200 of FIG. 2B.

According to various embodiments, the camera assembly 503 may include a dual-camera. The dual-camera may capture images of different parts through respective cameras and may combine the obtained images into one image so as to implement various images. For example, one camera 503a may focus on a subject, and the other camera 503b may capture an image of the surrounding background so as to use a wide-angle effect with a wider viewing angle for image processing, or an augmented reality effect may be implemented with three-dimensional data obtained using phase differences of images collected at different angles. As another example, the dual-camera may provide an image depending on long-range/short-range image capturing, with the support of optical zoom/digital zoom of each camera. For example, one camera 503a may acquire a wide-angle image including a main subject and the other camera 503b may acquire a telephoto image obtained by zooming in on the main subject. As another example, respective cameras may capture images of various distances using different focal lengths with higher image quality, and may change the magnification of captured images by zooming. As another example, in the dual-camera, each camera may support infrared image capturing in addition to normal image capturing. According to various embodiments, the biometric sensing unit 530 may be disposed at one side of the camera assembly 503, for example, at the lower end of the camera assembly 503. The biometric sensing unit 530 may include a biosensor 531 and an illumination unit 532, and may be integrated with the second plate 501, which is transparent. A separate window may be disposed in the area in which a biosensor and an illumination unit (e.g., a flash) are disposed. According to an embodiment of the disclosure, the biometric sensing unit 530 may be implemented such that respective areas of the second plate 501 are seamlessly connected without being disconnected since an isolation structure, which may occur due to a separate window or other components, is excluded, thereby simplifying the structure and reducing the manufacturing cost.

According to various embodiments, the second plate 501 on which the biometric sensing unit 530 is disposed may include glass and a print layer 504 including a hole corresponding to the transparent area. The transparent area may be configured to exclude an additional opaque print layer so that the biometric sensing unit 530 may recognize at least a portion of the user's body through the transparent area or light may be provided to the outside through the transparent area. As another example, a separate opaque print layer including an opening corresponding to the biosensor 860 may be formed such that the biometric sensing unit 530 is visually distinguishable from the outside. For example, the opaque print layer may be directly or indirectly attached to the inner face of the second plate 501, and may include at least one opening disposed in the camera assembly area or in the biosensor area. According to an embodiment of the disclosure, when the second plate 501 is viewed from the outside, the biometric sensing unit 530 is not physically distinguished from other areas, so that it is possible to provide a generally smooth flat design. Furthermore, the sensing unit 530 may provide a beautiful design by forming the visually distinguishable print layer.

Figure 8A:
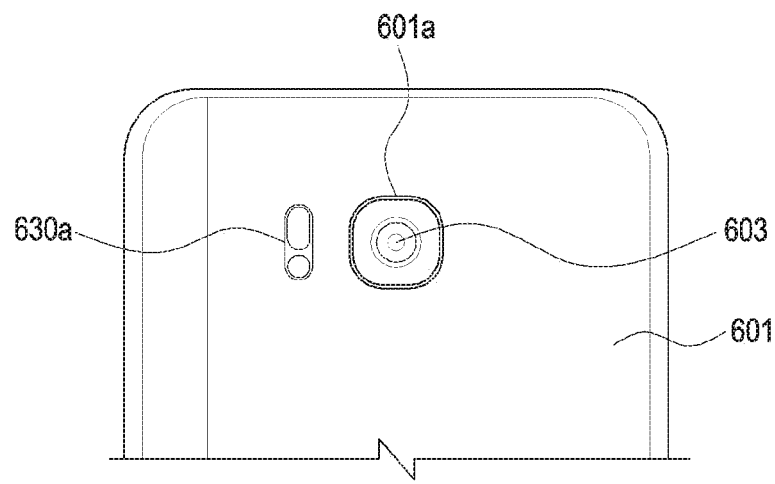
FIG. 8A and FIG. 8B is a front view illustrating an arrangement relationship between a camera assembly 603 and a biometric sensing unit 630 disposed on a second glass plate 601 according to various embodiments of the disclosure.
Figure 8B:
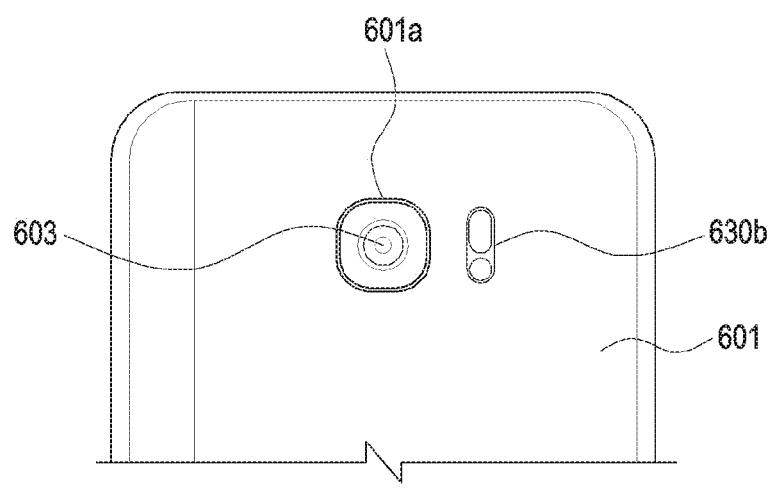

FIG. 8A and FIG. 8B is a front view illustrating an arrangement relationship between a camera assembly 603 and a biometric sensing unit 630 disposed on a second plate 601 according to various embodiments of the disclosure. The biometric sensing unit 630a or 630b including the second plate 601, the camera assembly 603, and the biosensor of the electronic device illustrated in FIGS. 8A and 8B may be partially or wholly the same as the biometric sensing unit 530 including the second plate 501, the camera assembly 503, and the biosensor of the electronic device 500 of FIG. 7.

Referring to FIGS. 8A and 8B, the biometric sensing unit 630a or 630b may disposed on the second plate 601 and may be located at various positions relative to the area in which the camera assembly 603 is disposed. FIG. 7 illustrates the biometric sensing unit 530 is disposed at the lower end of the hole 501a of the second plate 501 in which the camera assembly 503 is disposed. However, without being limited thereto, the biometric sensing unit 530 may be disposed in any of various areas as long as biometric recognition can be conveniently performed on the user. For example, referring to FIG. 8A, when viewed from above the second plate 601, the biometric sensing unit 630a may be disposed at the left side of the hole 601a in which the camera assembly 603 is disposed. As another example, referring to FIG. 8B, when viewed from above the second plate 601, the biometric sensing unit 630b may be disposed at the right side of the hole 601a in which the camera assembly 603 is disposed.

Figure 9:
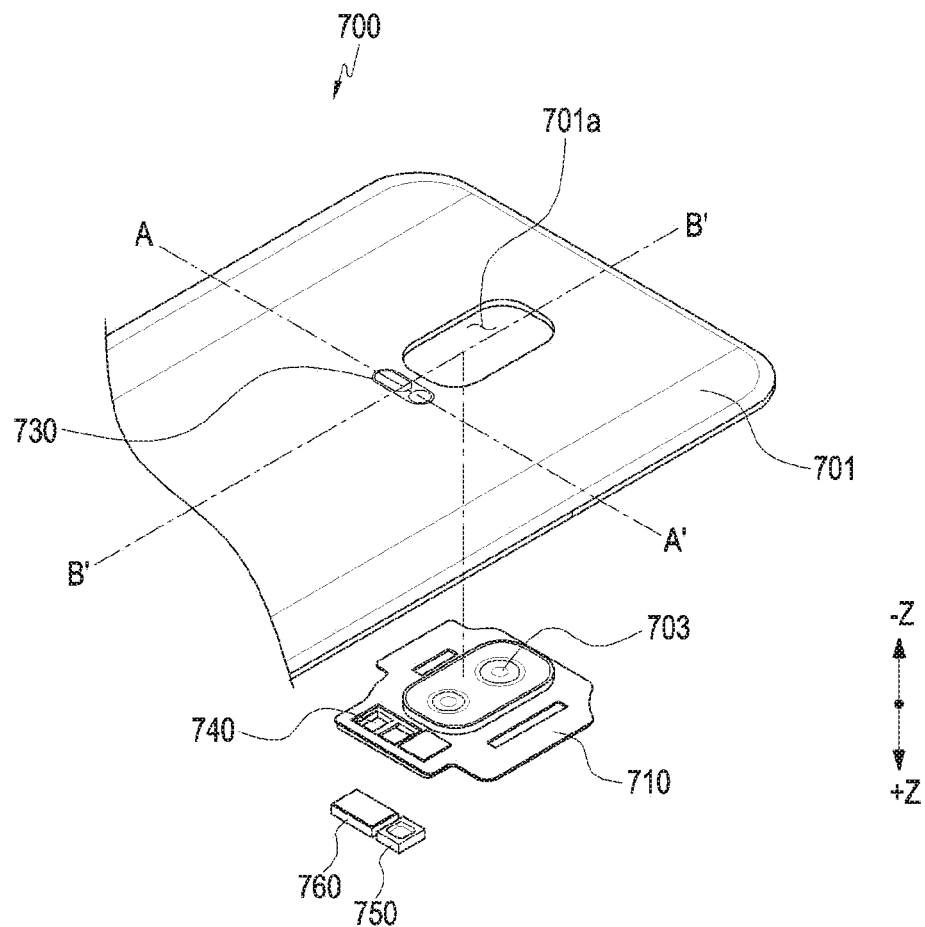
FIG. 9 is an exploded perspective view illustrating a bracket 710 mounted with a camera assembly 703 and a biometric sensing unit 730 and disposed on a second plate 701 having an opening 701a according to various embodiments of the disclosure.
Figure 10:
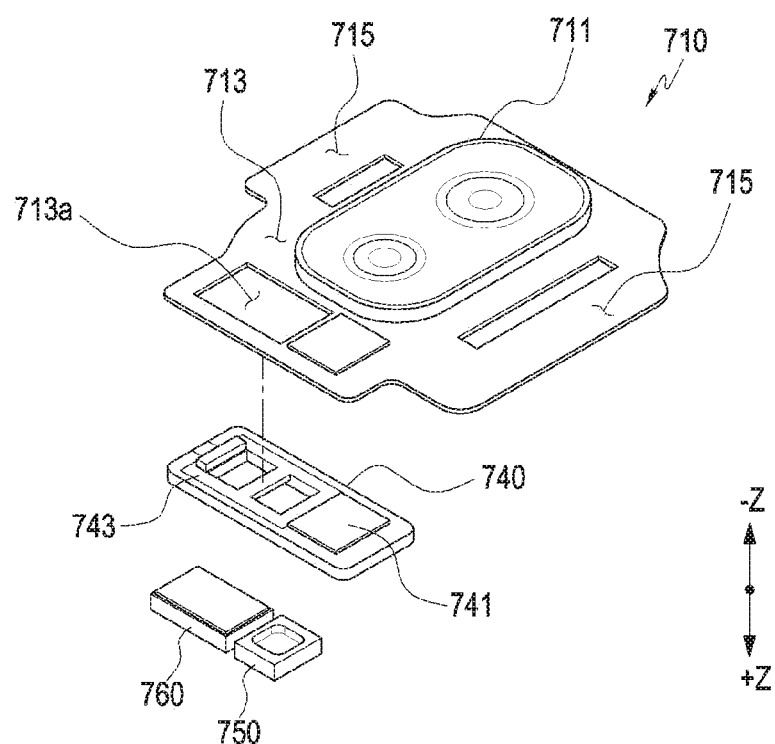
FIG. 10 is an exploded perspective view illustrating the bracket 710 and a light guide structure 740 according to various embodiments of the disclosure.

FIG. 9 is an exploded perspective view illustrating a bracket 710 mounted with a camera assembly 703 and a biometric sensing unit 730 and disposed on a second plate 701 having an opening 701a according to various embodiments of the disclosure. FIG. 10 is an exploded perspective view illustrating the bracket 730 and a light guide structure 740 according to various embodiments of the disclosure.

Referring to FIGS. 9 and 10, the electronic device 700 may include a second plate 701, a bracket 710 disposed on the second plate 701, a camera assembly 703, a light guide structure 740 disposed adjacent to the bracket 710, an illumination unit 750, and a biosensor 760. On the bracket 710, at least a portion of the camera assembly 703 may be disposed, or a separate window other than the camera assembly may be directly assembled. The structure of the second plate 701, the camera 703, the biosensor 760, and the illumination unit 750 of the electronic device illustrated in FIGS. 9 and 10 are partially or wholly the same as the structure of the second plate 501, the camera assembly 503, and the biometric sensing unit 530 of the electronic device 500 of FIG. 7.

According to various embodiments, in the electronic device 700, the second plate 701 made of a transparent glass material may be located on the rear face of the electronic device 700 so as to protect the internal components of the electronic device 700 from the external environments. The second plate 701 may include at least one hole 701*a* penetrating one face of the second plate 701. The camera assembly 703 or the biosensor 760 may be disposed in the hole 701*a* so as to be at least partially exposed to the outside. The camera assembly 703 may be a dual-camera as described above.

According to various embodiments, the bracket 710 is formed in a plate shape including the hole 701*a* of the second plate 701 and a peripheral area thereof, and may be disposed such that at least a portion thereof is exposed through the hole 701*a* in the second plate 701. The bracket 710 may provide a structure on which the camera 703 and the biometric sensing unit are capable of being seated or supported. In addition, the bracket 710 may exhibit a waterproof function for blocking fluid or foreign matter introduced from the outside by closing the opening area.

According to various embodiments, the bracket 710 may include a camera area 711 in which a camera 703 or a lens of the camera 703 is mounted, and a biometric sensing area 713 disposed adjacent to the camera area 711 and including the biosensor 760 and the illumination unit 750 disposed therein. In addition, the bracket 710 may include a peripheral area 715 formed around the camera area 711 and the biometric sensing area 713 so as to fix the entire bracket 710 to the second plate 701 to be in close contact with each other.

According to various embodiments, the camera area 711 of the bracket 710 may protrude in the second direction (−Z) with a size corresponding to the hole 701*a* in the second plate 701. The protruding camera area 711 may be exposed to the outside through the hole 701*a*, and a transparent window may be disposed in the protruding camera area 711. A camera lens or a camera may be disposed inside the window. According to various embodiments, the biometric sensing area 713 of the bracket 710 may extend from the camera area 711 to an area in which the biosensor 760 and the illumination unit 750 are disposed, and may include at least one opening 713*a*. At least a portion of the biosensor 760 or the illumination unit 750 may directly face the second plate 701 through the at least one opening 713*a*.

According to various embodiments, the electronic device 700 may include a light guide structure 740 disposed on the bracket 710 in the first direction (+Z). The light guide structure 740 may be manufactured in a shape corresponding to at least a portion of the biometric sensing area 713 of the bracket 710, and may be disposed directly facing the biometric sensing area 713. The light guide structure 740 may support the biosensor 760 and/or the illumination unit 750, and may guide the path of light transmitted or received by the biosensor 760 and/or the illumination unit 750.

According to an embodiment, the light guide structure 740 may include a first portion 741 corresponding to the illumination unit 750 and a second portion 743 corresponding to the biosensor 760. A shielding wall (the shielding wall 843 in FIG. 11), which is capable of distinguishing an optical path, may be formed between the first portion 741 and the second portion 743. The second portion 743 may be formed in an open shape so as to provide a passage through which light and/or sound waves pass from the biosensor 760. The second portion 743 may be formed in an annular strip shape surrounding at least one portion of the biosensor 760 when viewed from above the second plate 701. As an example, the first portion 741 may include a light guide structure made of a transparent material so as to guide light emitted from the illumination unit 750 providing a light source.

Figure 11:
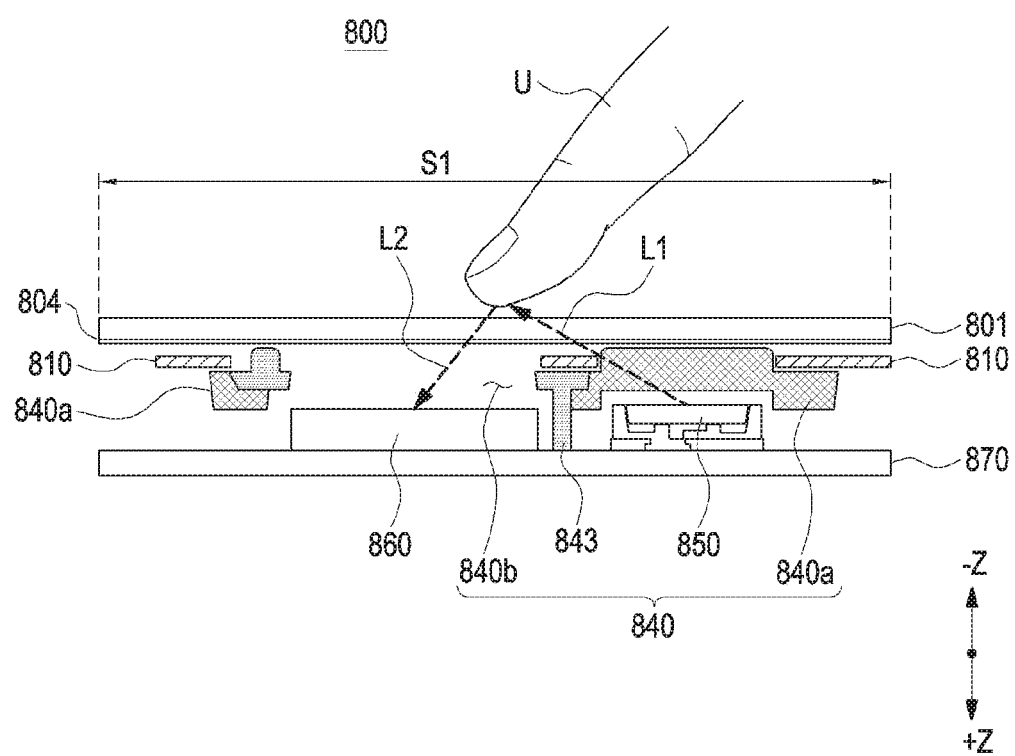
FIG. 11 is a cross-sectional view taken along line A-A' in FIG. 9, in which an area including a biosensor of the electronic device 700 of FIG. 9 according to various embodiments of the disclosure is illustrated.
Figure 12:
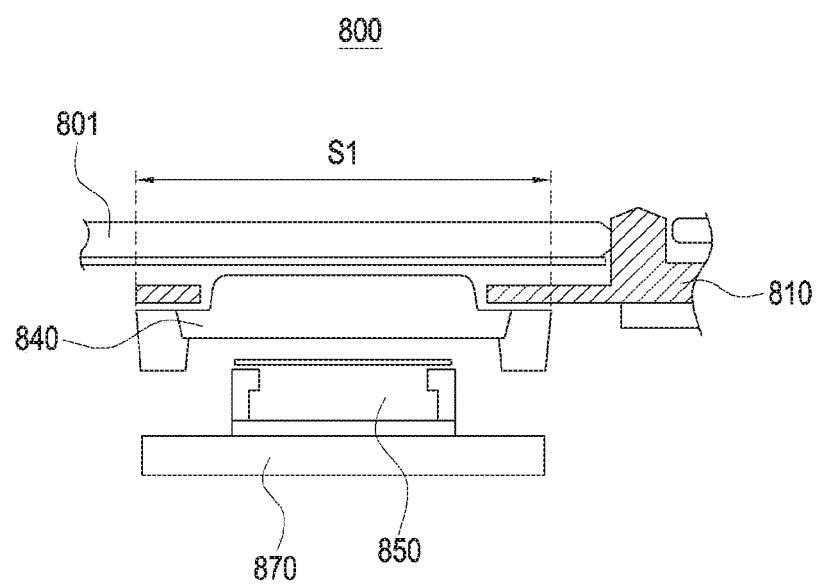
FIG. 12 is a cross-sectional view taken along line B-B' in FIG. 9, in which an area including a biosensor of the electronic device 700 of FIG. 9 according to various embodiments of the disclosure is illustrated.

FIG. 11 is a cross-sectional view taken along line A-A' in FIG. 9, in which an area including a biosensor of the electronic device 700 of FIG. 9 according to various embodiments of the disclosure is illustrated. FIG. 12 is a cross-sectional view taken along line B-B' in FIG. 9, in which an area including a biosensor of the electronic device 700 of FIG. 9 according to various embodiments of the disclosure is illustrated.

Referring to FIGS. 11 and 12, the biometric sensing area S1 of the electronic device 800 may include a second plate 801, a bracket 810 disposed on the second plate 801, a light guide structure 840 connected to the bracket 810, an illumination unit 850, and a biosensor 860. The structure of the second plate 801, the bracket 810, the light guide structure 840, the illumination unit 850, and the biosensor 860 of the electronic device illustrated in FIGS. 11 and 12 may be partially or wholly the same as the structure of the second plate 701, the bracket 710, the light guide structure 740, the illumination unit 750, and the biosensor 760 of the electronic device 700 of FIGS. 9 and 10.

According to various embodiments, in the biometric sensing area S1, the bracket 810 and the light guide structure 840 are stacked in the first direction (+Z) with respect to the second plate 801, the biosensor 860 may disposed below one area of the bracket 810 and the light guide structure 840, and the illumination unit 850 may be disposed below the other area of the bracket 810 and the light guide structure 840.

According to various embodiments, the second plate 801 may be made of transparent glass including at least one hole as described above, and an additional opaque print layer may not be formed in the biometric sensing area S1 such that the biometric sensing area S1 is exposed to the outside. As another example, a separate opaque print layer 804 including an opening corresponding to the biosensor 860 may be formed such that the biometric sensing area S1 is visually distinguishable from the outside compared to the other area of the second plate 801. For example, the opaque print layer 804 may be directly or indirectly attached to the inner face of the second plate 501, and may include a first opening disposed in the camera assembly area and a second opening disposed in the biosensor area. The first opening and the second opening may be disposed adjacent to each other in the longitudinal direction of the second plate 501. For example, the second opening disposed above the biosensor may be disposed within 150 mm in the longitudinal direction from the first opening disposed above the camera assembly. At least one hole in the second plate 501 may overlap the first opening, but may not overlap the second opening.

According to various embodiments, the bracket 810 may extend from the area in which the camera assembly (the camera assembly 703 in FIG. 9) is disposed to support respective electronic components, and the light guide structure 840 may guide the paths of the light and/or sound waves transmitted to/received from the biosensor 860 and/or may guide the path of the light emitted from the illumination unit 850.

According to various embodiments, the electronic device 800 may include the biosensor 860 for sensing biometric information of the user through an area of the second plate 801. The biosensor may be a fingerprint sensor or a Heart Rate Monitor (HRM) sensor.

According to an embodiment, the fingerprint sensor may be implemented in an electrostatic type by forming a sensible electrode on the surface of the second plate 801. The electrostatic-type fingerprint sensor may be disposed inside the second plate 801 so as to be adjacent to the camera assembly (the camera assembly 703 in FIG. 9), and the second plate 801 may include at least one hole in the area corresponding to the fingerprint sensor such that the fingerprint sensor is exposed to the outside to be capable of being touched with the user's body.

According to an embodiment, the electrostatic-type fingerprint sensor may be exposed to the outside through hole in the second plate 801 like the camera assembly. For example, the fingerprint sensor and a heart rate measurement device sensor may be arranged to correspond to the upper and lower areas or in the left and right regions with reference to the camera assembly. Unlike the camera assembly or the fingerprint sensor, the heart rate measurement device sensor may be provided inside an area of the second plate 801 in which no hole is provided.

As another example, at least one hole may also be formed in an area of the bracket 810 disposed between the at least one hole in the second plate 801 and the fingerprint sensor so as to be capable of recognizing the user's biometric information via the fingerprint sensor. As another example, the fingerprint sensor of the electrostatic type may be disposed in the vicinity of the bracket 810, for example, below the opening in the second plate 801 so as to be capable of recognizing the user's biometric information.

According to an embodiment, the fingerprint sensor may be implemented in an ultrasonic manner by forming an ultrasonic transmitter/receiver adjacent to the layer in which the fingerprint sensor is disposed.

According to an embodiment, the fingerprint sensor may be constituted with an optical fingerprint sensor for sensing the user's fingerprint using light emitted from a light source disposed adjacent to the fingerprint sensor. The emitted light may be implemented through the light emitted from a light source (e.g., an IR LED or the like) using the illumination unit 850 serving as a flash or separately implemented inside the electronic device 800. In the following description, a configuration for sensing the fingerprint of a user using light provided via the illumination unit 850 will be described.

According to various embodiments, the illumination unit 850, which provides light, may be disposed between a PCB 870 and the light guide structure 840, and may be electrically connected to the PCB 870 so as to emit light. The PCB 870 may be an FPCB. The illumination unit 850 may be, for example, an LED module, and may radiate light to one face of the light guide structure 840. For example, the light emitted from the illumination unit 850 may have various colors. For example, the emitted light may be light in the wavelength range of visible light or infrared light.

According to various embodiments, the light guide structure 840 disposed above the illumination unit 850 may be a first portion 840a of the light guide structure, and the first portion 840a may be disposed such that at least a portion thereof protrudes to the opening in the bracket 810. The first portion 840a may guide the light received from the illumination unit 850 to the second plate 801. The light incident into the first portion 840a may form a first path L1 including total internal reflection. For example, the first path L1 of the light of the first portion 840a on which the light of the illumination unit 850 is incident may provide at least one total reflection, and may change the path of a part of the light provided from the illumination unit 850 to be directed right-upwards or left-upwards (upwards towards the position at which the fingerprint sensor is located).

According to various embodiments, the first portion 840a may be fabricated in a shape in which respective faces, which form the first portions 840a, have different lengths and the angles between the faces have different slopes, and may be made of a material that provides high transmissivity. For example, the light guide structure 840 may have transmissivity of about 90% or more, and may be made of a material including transparent silicon or acrylic. The first portion 840a provides a space for the first path L1 of light in a single form through an incident face for receiving the light emitted from the illumination unit 850 and an outgoing face for providing the incident light to the second plate 801. However, without being limited thereto, the first portion may be provided in various forms depending on the internal structure of the electronic device, and may be formed of more than two faces.

According to various embodiments, the light guide structure 840 disposed above the fingerprint sensor may be a second portion 840b of the light guide structure 840, and at least a portion of the second portion 840b may be open so as to guide the light reflected from the fingerprint of the user to the fingerprint sensor. The light incident into the second portion 840b may form a second path L2 of light, and may be filled with air to reduce a medium change.

According to various embodiments, at least one shielding wall 843 may be provided between the first portion 840a and the second portion 840b to prevent mutual interference between the illumination unit 850 and the fingerprint sensor. The shielding wall 843 is capable of blocking the direct path, through which the light emitted from the illumination unit 850 is directly transmitted to the fingerprint sensor, so as to prevent interference light other than the reflected light from being transmitted to the fingerprint sensor.

Referring to the advancing path of light according to various embodiments, the light passing through the first portion 840a may be directed toward the fingerprint of the user U that is in contact with the biometric sensing area S1 of the second plate 801. The light is reflected by a ridge and/or a valley of the user's fingerprint, and the reflected light is able to reach the fingerprint sensor. For example, the user's fingerprint placed in the biometric sensing area S1 of the second plate 801 has an irregular face in the shape of a valley and/or a ridge, thereby being divided into an area, which is in contact with the second plate 801 and an area, which is not in contact with the second plate 801. At this time, in the area of the user's fingerprint, which is not in contact with the second plate 801, the light transmitted along the first path L1 is totally reflected so as to progress again, but in the area of the user's fingerprint, which is in contact with the second plate 801, a part of the light may be absorbed into the user's fingerprint and the remaining part of the light may be scattered and reflected. Therefore, the light incident on the second plate 801, which is not in contact with the user's fingerprint, is totally reflected and progresses toward the fingerprint sensor through the second path L2. However, the light incident on the second plate 801, which is in contact with the user's fingerprint, cannot progress to the fingerprint sensor by being absorbed, refracted, or scattered.

According to various embodiments, the fingerprint sensor may be disposed under the second plate 801, and may receive the light provided to the second plate 801 so as to sense the user's fingerprint information. The fingerprint sensor may be disposed on the upper face of the PCB 870, and may be electrically connected to the PCB 870.

According to various embodiments, the fingerprint sensor may focus the light totally reflected by the second plate 801, and a lens having a short focal length may be used in order to miniaturize an optical scanning device. As another example, the fingerprint sensor may be formed of an array lens to correspond to the size of an image to be scanned, and the array lens may be formed in a matrix structure.

Figure 13:
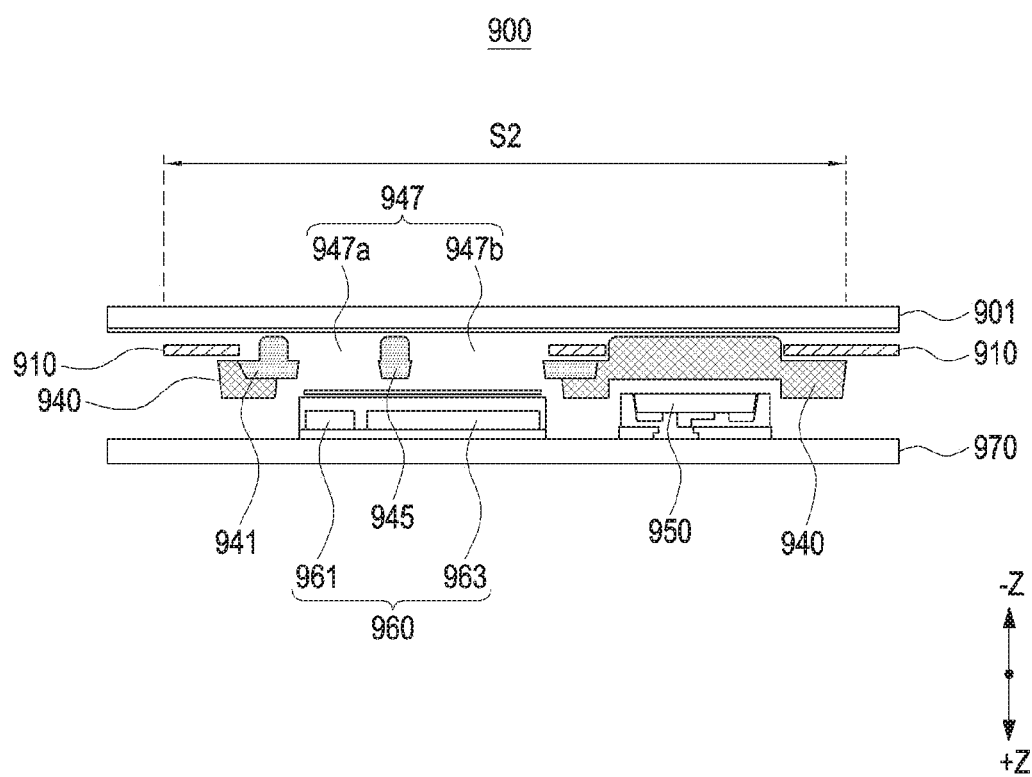
FIG. 13 is a cross-sectional illustrating an area in which a biosensor of an electronic device 900 according to another embodiment of the disclosure is included.

FIG. 13 illustrates an area in which a biosensor of an electronic device 900 according to another embodiment of the disclosure is included.

Referring to FIG. 13, the biometric sensing area S2 of the electronic device 900 may include a second plate 901, a bracket 910 disposed on the second plate 901, a light guide structure 940, an illumination unit 950, and a biosensor 960. The structure of the second plate 901, the bracket 910 disposed on the second plate 901, the light guide structure 940, the illumination unit 950, and the biosensor 960 of the electronic device 900 illustrated in FIG. 13 may be partially or wholly the same as the structure of the second plate 701, the bracket 710, the light guide structure 740, the illumination unit 750, and the biosensor 760 of the electronic device 700 of FIGS. 9 and 10.

According to various embodiments, in the biometric sensing area S2, the bracket 910 and the light guide structure 940 are stacked in the first direction (+Z) with respect to the second plate 901, the biosensor 960 may disposed below one area of the bracket 910 and the light guide structure 940, and an illumination unit 950 may be disposed below the other area of the bracket 910 and the light guide structure 940.

According to various embodiments, the second plate 901 may be made of transparent glass, and an additional print layer may not be formed in the biometric sensing area S2 such that the biometric sensing area S2 is exposed to the outside. As another example, the bracket 910 may extend from the area in which the camera assembly (the camera assembly 503 in FIG. 7) is disposed to support respective electronic components, and the light guide structure 940 may guide the paths of the light or sound waves transmitted to/received from the biosensor 960 and/or may guide the path of the light emitted from the illumination unit 950.

According to various embodiments, the electronic device 900 may include the biosensor 960 for sensing biometric information through an area of the second plate 901. For example, the biosensor 960 may be a sensor disposed between the PCB 970 and the optical guide structure 940 to collect or measure one or more biometric signals from the user. The biosensor module may collect raw data for measuring one or more of the user's blood pressure, blood flow, heart rate (HRM, HRV), body temperature, respiration rate, oxygen saturation, cardiac tone, blood sugar, waist size, height, weight, body fat, calorie consumption, brainwaves, voice, skin resistance, electromyogram, electrocardiogram, gait, ultrasound image, sleep state, facial expression (face), pupil dilation, or eye blink.

According to an embodiment, a pulse wave signal obtained through the HRV or HRM sensor may be a biometric signal. The electronic device may obtain primary biometric information such as an average heart rate or a heart rate distribution by analyzing a biometric signal, and may obtain secondary biometric information, such as a higher level of stress state or vascular aging by processing the biometric information.

According to an embodiment, when an electronic device (e.g., the electronic device 101 or 201 in FIG. 1) having the biosensor embedded therein transmits a biometric signal to a remote device (e.g., the electronic device 104 in FIG. 1) or a server (e.g., the server 106 in FIG. 1) via a wired network, a wireless network, or a direct connection, the remote device or the server that receives the biometric signal may process the biometric signal so as to generate biometric information. According to an embodiment, when the electronic device (e.g., the electronic device 101 or 201 in FIG. 1) having the biosensor module embedded therein generates primary biometric information and transmits the generated biometric information to a remote device or a server, secondary biometric information may be generated in the remote device or the server.

According to an embodiment, the biosensor may be an HRM. The biosensor 960 may sense contraction/expansion of blood vessels in the skin of a human body on the basis of reflection of light according to a change in a blood volume in the blood vessels. The processor (e.g., the processor 120 in FIG. 1) may receive an electrical signal of the biosensor 960 and may calculate heartbeat.

According to various embodiments, the biosensor 960 may include at least one light-emitting element 961 for emitting light and a light-receiving element 963 for receiving light reflected from the user's body. The at least one light-emitting element 961 may emit light towards the second plate 901. For example, the light-emitting element 961 may be an LED module, and the light emitted from the light-emitting element 961 may emit light of various colors. The emitted light may have a wavelength in the range of about 380 nm to 800 nm. As another example, the light emitted from the light-emitting element 961 may be green light, and may have a wavelength in the range of about 492 nm to 575 nm.

According to various embodiments, the light-receiving element 963 is disposed on the same plane as the light-emitting element 961, and when the light emitted from the light-emitting element 961 is reflected by the user's body, the light-receiving element 963 may receive the reflected light and may convert the light into current. For example, in order to measure the user's heartbeat, when a part of the light emitted from the light-emitting element 961 is reflected by the blood flow in the blood vessels of the user and returned to the light-receiving element 963, the light-receiving element 963 may convert the light signal into a current signal. According to an embodiment of the disclosure, an example in which one light-emitting element and one light-receiving element are arranged in parallel on the same plane has been described. However, the disclosure is not limited thereto, and various numbers and arrangements of light-emitting elements and light-receiving elements may be implemented in order to efficiently receive the user's biometric information.

According to various embodiments, the light guide structure 940 is stacked with the bracket 910 at a portion 941 thereof, and may include at least one opening 947 so as to expose the light-emitting element 961 and the light-receiving element 963 in the second direction (−Z). In addition, the light guide structure 940 may include at least one shielding wall 945 to prevent mutual interference between the light-emitting element 961 and the light-receiving element 963.

According to various embodiments, the portion 941 of the light guide structure 940 may have a plate shape including multiple openings 947, and the openings 947 may be formed to penetrate the upper and lower faces of the light guide structure 940. The multiple openings 947 may include a first opening 947*a* and at least one second opening 947*b* having a size different from that of the first opening 947*a*.

According to various embodiments, the light emitted from the light-emitting element 961 disposed inside the first opening 947*a* should be directly transmitted to the user, and the light reflected by the user should be transmitted to the light-receiving element 963 that is arranged parallel to the light-emitting element 961. The shielding wall 945 is capable of blocking the direct path, through which the light emitted from the light-emitting element 961 is directly transmitted to the light-receiving element 963, so as to prevent interference light other than the reflected light from reaching the light-receiving element 963.

According to various embodiments, the first opening 947a in the light guide structure 940 may be formed in a shape corresponding to the shape of the light-emitting element 961, and the second opening 947b in the light guide structure 940 may be formed in a shape corresponding to the shape of the light-receiving element 963. Although the numbers and shapes of the first openings 947a and the second openings 947b have been disclosed according to an embodiment of the disclosure, but the disclosure is not limited to the numbers and shapes of the first openings 947a and the second openings 947b. The first openings 947a and the second openings 947b may be variously modified in number and shape to correspond to the light-emitting elements and the light-receiving elements.

In addition to the foregoing, FIG. 11 is applicable to the configuration of the illumination unit 940 and the electrical connection relationship with the PCB 670 disposed at the lower portion.

Figure 14A:
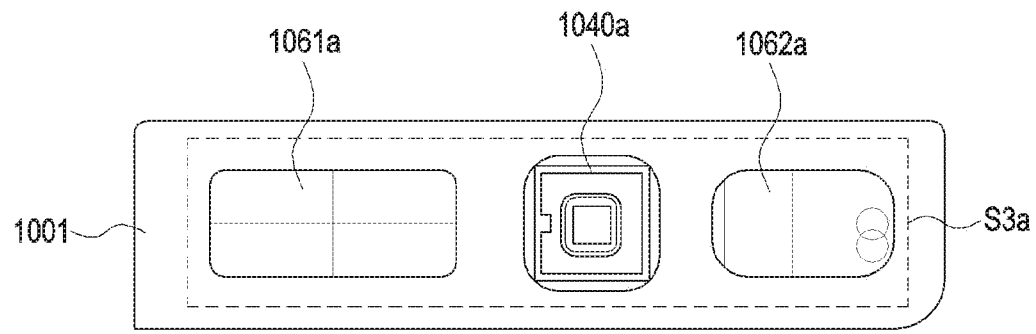
FIG. 14A to 14C are views illustrating various arrangement relationships of multiple biosensors 1061a to 1061c and 1062a to 1062c and illumination units 1040a to 1040c disposed in the biometric sensing areas S3a to S3c of a second plate according to various embodiments of the disclosure.
Figure 14B:
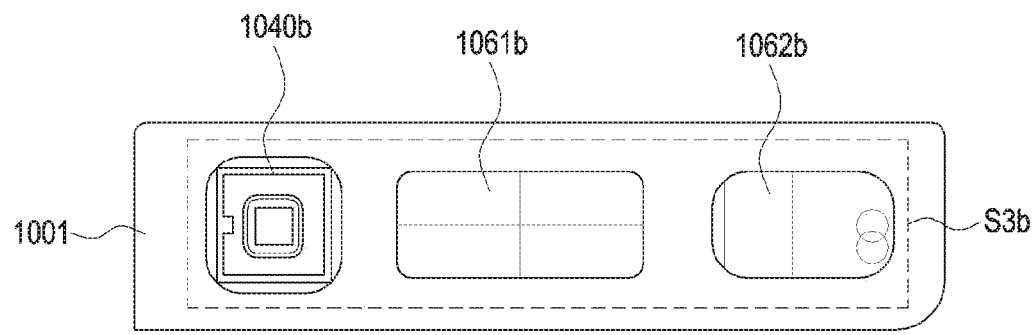
Figure 14C:
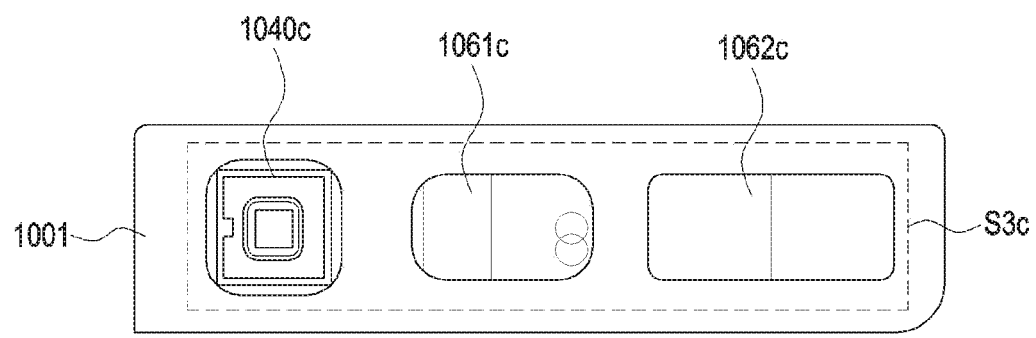

FIGS. 14A to 14C are views illustrating various arrangement relationships of multiple biosensors 1061a to 1061c and 1062a to 1062c and illumination units 1040a to 1040c disposed in the biometric sensing areas S3a to S3c of a second plate according to various embodiments of the disclosure.

Referring to FIGS. 14A to 14C, the biometric sensing areas S3a to S3c of the electronic device may include a second plate 1001, multiple biosensors 1061a to 1061c and 1062a to 1062c disposed on the second plate 1001, and illumination units 1040a to 1040c. The structure of the second plate 1001, the multiple biosensors 1061a to 1061c and 1062a to 1062c, and the illumination units 1040a to 1040c of the electronic device illustrated in FIGS. 14A to 14C may be partially or wholly the same as the structure of the second plate 701, the illumination unit 750, and the biosensor 760 of the electronic device 700 of FIGS. 9 and 10.

According to various embodiments, the biosensors 1061a to 1061c and 1062a to 1062c disposed in the biometric sensing areas S3a to S3c of the second plate 1001 may include fingerprint sensors 1061a to 1061c and HRM sensors 1062a to 1062c. In addition, the illumination units 1040a to 1040c may be disposed on the same plane as the fingerprint sensors 1061a to 1061c and HRM sensors 1062a to 1062c.

Referring to FIG. 14A, in the configuration of the biometric sensing area S3a of the second plate 1001 in which sensors and an illumination unit are arranged, the fingerprint sensor 1061a, the illumination unit 1040a, and the HRM sensor 1062a may be sequentially arranged from the left.

According to an embodiment, the fingerprint sensor 1061a may be constituted with an optical fingerprint sensor 1061a for sensing the user's fingerprint using light emitted from a light source disposed adjacent to the fingerprint sensor 1061a. The emitted light may be implemented through the light emitted from a light source (e.g., an IR LED or the like) using the illumination unit 1040a serving as a flash or separately implemented inside the electronic device. According to another example, at least one shielding wall may be disposed between the fingerprint sensor 1061a and the illumination unit 1040a so as to prevent optical interference with each other.

According to an embodiment, the HRM sensor 1062a may be disposed on a side portion corresponding to the fingerprint sensor 1061a with reference to the illumination unit 1040a, and may sense contraction/expansion of blood vessels in the skin of a human body on the basis of the reflection of light caused due to a change in an amount of blood in the blood vessels. The processor (e.g., the processor 120 in FIG. 1) may receive an electrical signal of the HRM sensor 1062a and may calculate heartbeat. According to another example, at least one shielding wall may be disposed between the HRM sensor 1062a and the illumination unit 1040a so as to prevent optical interference with each other. The descriptions of the configurations of the fingerprint sensor, the illumination unit, and the HRM sensor of FIGS. 11 to 13 are applicable to the detailed descriptions of the corresponding configurations.

Referring to FIG. 14B, in the configuration of the biometric sensing area S3b of the second plate 1001 in which sensors and an illumination unit are arranged, the illumination unit 1040b, the fingerprint sensor 1061b, and the HRM sensor 1062b may be sequentially arranged from the left. According to an embodiment, between the illumination unit 1040b and the fingerprint sensor 1061b and/or between the fingerprint sensor 1061b and the HRM sensor 1062b, at least one shielding wall (not illustrated) may be disposed. The descriptions of the configurations of the fingerprint sensor, the illumination unit, and the HRM sensor of FIGS. 11 to 14A are applicable to the detailed descriptions of the corresponding configurations.

Referring to FIG. 14C, in the configuration of the biometric sensing area S3c of the second plate 1001 in which sensors and an illumination unit are arranged, the illumination unit 1040c, the HRM sensor 1062c, and the fingerprint sensor 1061c may be sequentially arranged from the left. According to an embodiment, between the illumination unit 1040c and the HRM sensor 1062c and/or between the fingerprint sensor 1061c and the HRM sensor 1062c, at least one shielding wall (not illustrated) may be disposed. The descriptions of the configurations of the fingerprint sensor, the illumination unit, and the HRM sensor of FIGS. 11 to 14A are applicable to the detailed descriptions of the corresponding configurations.

According to an embodiment of the disclosure, the illumination units 1040a to 1040c, the HRM sensors 1062a to 1062c, and the fingerprint sensors 1061a to 1061c may be arranged parallel to each other in the biometric sensing areas S3a to S3c of the second plate. With this structure, it is possible to simultaneously provide individual authentication (e.g., fingerprint authentication) and human body measurement (e.g., data acquisition) in one operation.

Figure 15:
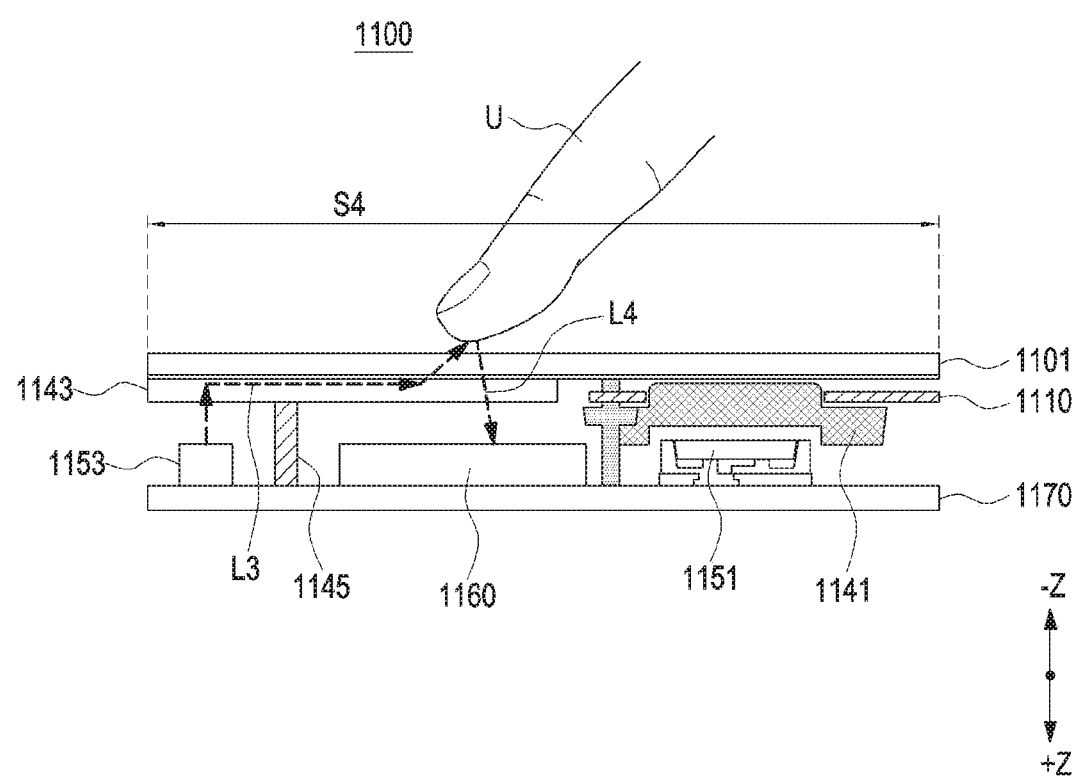
FIG. 15 is a cross-sectional view illustrating the structure of electronic components included in a biometric sensing area S4 of an electronic device 1100 according to various embodiments of the disclosure.

FIG. 15 is a cross-sectional view illustrating the structure of electronic components included in a biometric sensing area S4 of an electronic device 1100 according to various embodiments of the disclosure.

Referring to FIG. 15, the biometric sensing area S4 of the electronic device 1100 may include a second plate 1101, a bracket 1110 disposed on the second plate 1101, a first illumination unit 1151, a second illumination unit 1153, and a biosensor 1160. The structure of the second plate 1101, the bracket 1110, the light guide structures 1141 and 1143, the illumination units 1151 and 1153, and the biosensor 1160 of the electronic device 1100 illustrated in FIG. 15 may be partially or wholly the same as the structure of the second plate 701, the bracket 710, the light guide structure 740, the illumination unit 750, and the biosensor 760 of the electronic device 700 of FIGS. 9 and 10.

According to various embodiments, in the biometric sensing area S4, the bracket 1110 and the light guide structures 1141 and 1143 are stacked in the first direction (+Z) with respect to the second plate 1101, the biosensor 1160 and the second illumination unit 1153 may disposed below one area of the bracket 1110 and the light guide structures 1141 and 1143, and the first illumination unit 1151 may be disposed below the other area of the bracket 1110 and the light guide structures 1141 and 1143.

According to various embodiments, as described above, the second plate 1101 may be made of transparent glass, and an additional print layer may not be formed in the biometric sensing area S4 such that the biometric sensing area S4 is exposed to the outside. As another example, the bracket 1110 may extend from the area in which the camera is disposed to support respective electronic components, and the light guide structures 1141 and 1143 may guide the paths of the light and/or sound waves transmitted to/received from the biosensor 1160 and/or may guide the path of the light emitted from the first and second illumination units 1153.

According to various embodiments, the electronic device 1100 may include the biosensor 1160 for sensing biometric information of the user through an area of the second plate 1101. The biosensor may include a fingerprint sensor and/or an HRM sensor.

According to an embodiment, the fingerprint sensor may be constituted with an optical fingerprint sensor for sensing the user's fingerprint using light emitted from a light source disposed adjacent to the fingerprint sensor. The emitted light may be implemented through the light emitted from a light source (e.g., the second illumination unit 1153) implemented separately from the first illumination unit 1151 serving as a flash. In the following description, a configuration for sensing the user's fingerprint using light provided via the illumination unit 1153 will be described.

According to various embodiments, the second illumination unit 1153, which provides light used for the second sensor 1160, may be disposed between the PCB 1170 and the light guide structures 1141 and 1143, and may be electrically connected to the PCB 1170 so as to emit light. The PCB 1170 may be an FPCB. The second illumination unit 1153 may be positioned at a predetermined distance from the first illumination unit 1151 with the fingerprint sensor 1160 therebetween, and may be disposed on one side of the optical guide structures 1141 and 1143. For example, the second illumination unit 1153 may be, for example, an LED module, and the light emitted from the second illumination unit 1153 may emit light of various colors. For example, the emitted light may be light in the wavelength range of visible light or infrared light.

According to various embodiments, the second light guide structure 1143 disposed above the second illumination unit 1153 may guide the light received from the second illumination unit 1153 to the second plate 1101. The light incident into the second light guide structure 1143 may form a first path L3 including total internal reflection. For example, the first path L3 of the light of the second light guide structure 1143 on which the light of the second illumination unit 1153 is incident may provide at least one total reflection, and may change the path of a part of the light provided from the second illumination unit 1153 to be directed right-upwards or left-upwards (upwards towards the position at which the fingerprint sensor is located).

According to various embodiments, the second light guide structure 1143 disposed above the fingerprint sensor 1160 may guide the light reflected from the fingerprint of the user U to the fingerprint sensor 1160. The light incident into a portion of the second light guide structure 1143 may form a second path L4 of light, and the peripheral area of the fingerprint sensor 1160 may be filled with air to reduce a medium change.

According to various embodiments, between the second illumination unit 1153 and the second fingerprint sensor 1160, at least one shielding wall 1145 may be disposed so as to prevent mutual interference between the second illumination unit 1153 and the fingerprint sensor 1160. The shielding wall 1145 is capable of blocking the direct path, through which the light emitted from the second illumination unit 1153 is transmitted to the fingerprint sensor 1160, so as to prevent interference light other than the reflected light from being transmitted to the fingerprint sensor.

Figure 16:
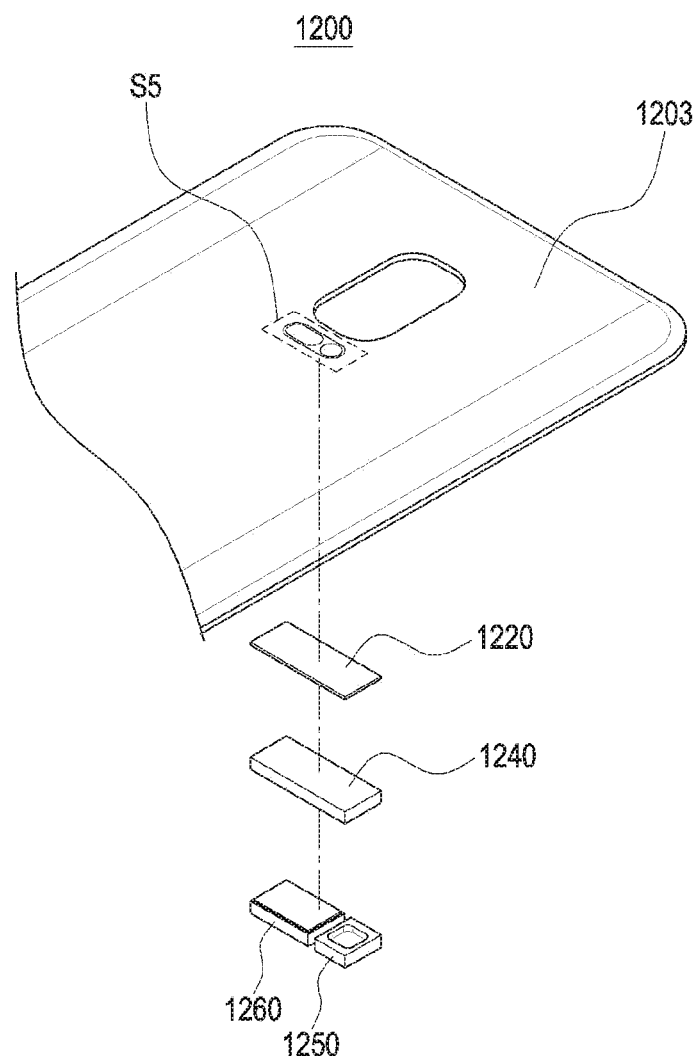
FIG. 16 is an exploded perspective view illustrating a biometric sensing area S5 in which a light guide structure 1240 disposed in a second plate 1201 of an electronic device 1200 according to various embodiments of the disclosure.
Figure 17:
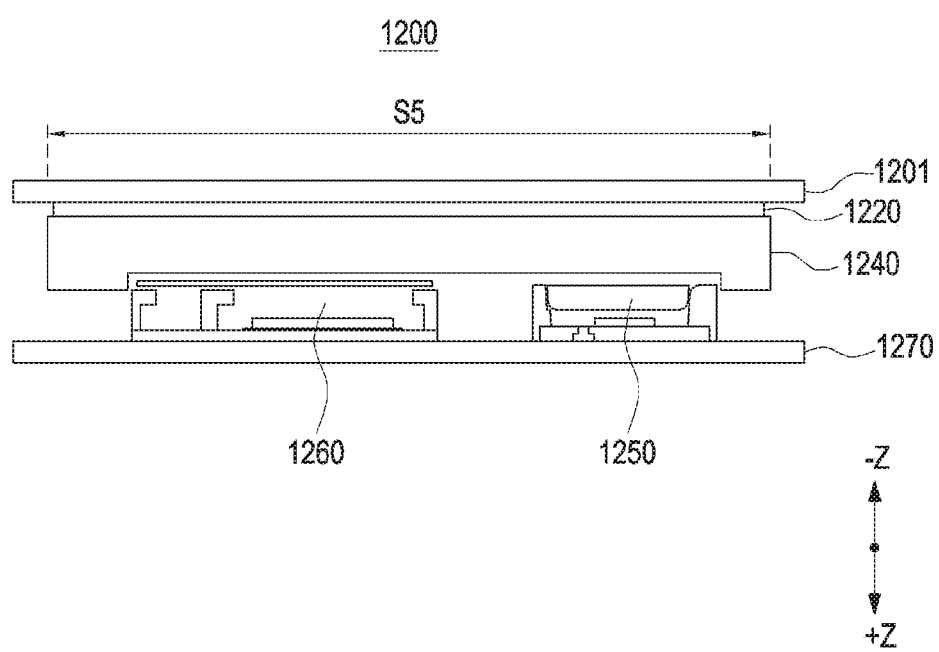
FIG. 17 is a cross-sectional view illustrating a biometric sensing area S5 in which a light guide structure 1240 is disposed in a second plate 1201 of the electronic device 1200 according to various embodiments of the disclosure.

FIG. 16 is an exploded perspective view illustrating a biometric sensing area S5 in which a light guide structure 1240 disposed in a second plate 1201 of an electronic device 1200 according to various embodiments of the disclosure. FIG. 17 is a cross-sectional view illustrating a biometric sensing area S5 in which a light guide structure 1240 disposed in a second plate 1201 of the electronic device 1200 according to various embodiments of the disclosure.

Referring to FIGS. 16 and 17, the biometric sensing area S5 of the electronic device 1200 may include a second plate 1201, a light guide structure 1240 disposed on the second plate 1201, an illumination unit 1250, and a biosensor 1260. The structure of the second plate 1201, the light guide structure 1240, the illumination unit 1250, and the biosensor 1260 of the electronic device 1200 illustrated in FIGS. 16 and 17 may be partially or wholly the same as the structure of the second plate 701, the light guide structure 740, the illumination unit 750, and the bio sensor 760 of the electronic device 700 of FIGS. 9 and 10.

According to various embodiments, in the electronic device 1200, the second plate 1201 made of a transparent glass material may be located on the rear face of the electronic device 1200 so as to protect the electronic device 1200 from the external environments.

According to various embodiments, in the biometric sensing area S5, the dielectric layer 1220 and the light guide structure 1240 are stacked in the first direction (+Z) with respect to the second plate 1201, the biosensor 1260 may be disposed below one area of the light guide structure 1240, and the illumination unit 1250 may be disposed below the other area of the light guide structure 1240.

According to various embodiments, the electronic device 1200 may include the biosensor 1260 for sensing biometric information of the user through an area of the second plate 1201. The biosensor may include a fingerprint sensor and/or an HRM sensor.

According to various embodiments, the illumination unit 1250, which provides light, may be disposed between a PCB 1270 and the light guide structure 1240, and may be electrically connected to the PCB 1270 so as to emit light. The PCB 1270 may be an FPCB. The illumination unit 1250 may be, for example, an LED module, and may radiate light to one face of the light guide structure 1240. For example, the light emitted from the illumination unit 1250 may have various colors. For example, the emitted light may be light in the wavelength range of visible light or infrared light.

According to various embodiments, a dielectric layer 1220 may be provided between the second plate 1201 and the light guide structure 1240. The dielectric layer 1220 may be disposed to be in contact with the second plate 1201, and may include, for example, silicon, air, foam, a membrane, Optical Clear Adhesive (OCA), sponge, rubber, ink, or a polymer (PC(polycarbonate) or PET(poly ethylene terephthalate)). According to various embodiments, the dielectric layer 1220 may be used as an adhesive of the second plate 1201 and the light guide structure 1240. For example, the dielectric layer 1220 may be bonded to the second plate 1201 through a lamination process. As another example, the dielectric layer 1220 may cover a gap between the illumination unit 1250 and the biosensor 1260 and the second plate 1201 that occurs due to different heights in the Z-axis direction. Accordingly, it is possible to reduce the loss of light emitted from the illumination unit 1250 or received by the biosensor 1260, thereby improving the performance of the sensor. Detailed descriptions of FIGS. 10 to 12 are applicable to the corresponding configurations.

Figure 18:
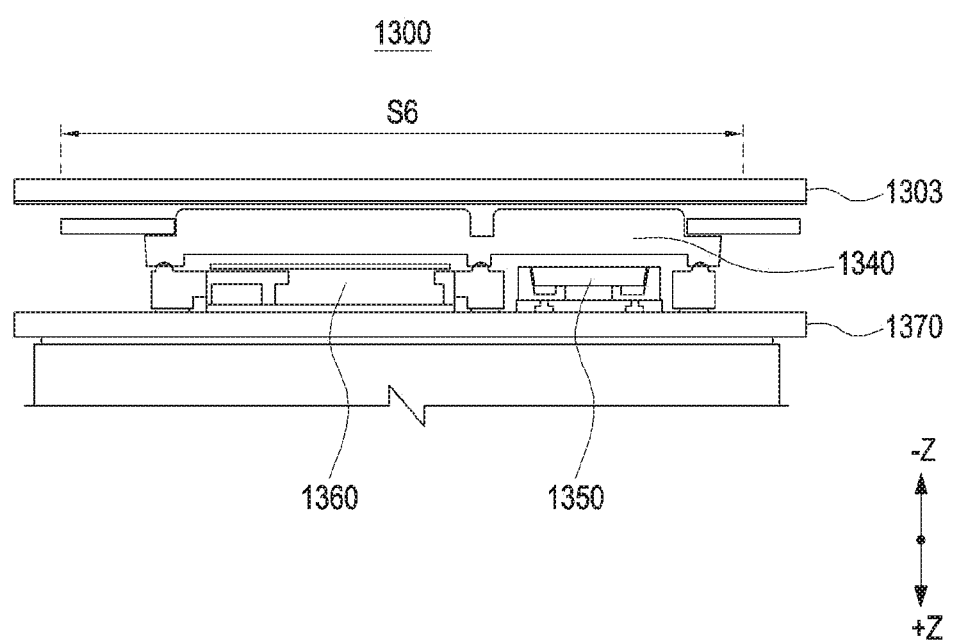
FIG. 18 is a cross-sectional view illustrating a biometric sensing area S6 in which a light guide structure 1340 is disposed in a second plate 1301 of an electronic device 1300 according to various embodiments of the disclosure.

FIG. 18 is a cross-sectional view illustrating a biometric sensing area S6 in which a light guide structure 1340 is disposed in a second plate 1301 of an electronic device 1300 according to various embodiments of the disclosure.

Referring to FIG. 18, the biometric sensing area S6 of the electronic device 1300 may include a second plate 1301, a light guide structure 1340 disposed on the second plate 1301, an illumination unit 1350, and a biosensor 1360. The structure of the second plate 1301, the light guide structure 1340, the illumination unit 1350, and the biosensor 1360 of the electronic device 1300 illustrated in FIG. 18 may be partially or wholly the same as the structure of the second plate 701, the light guide structure 740, the illumination unit 750, and the biosensor 760 of the electronic device 700 of FIGS. 9 and 10.

According to various embodiments, in the electronic device 1300, the second plate 1301 made of a transparent glass material may be located on the rear face of the electronic device 1300 so as to protect the electronic device 1300 from the external environments.

According to various embodiments, in the biometric sensing area S5, the dielectric layer 1320 and the light guide structure 1340 are stacked in the first direction (+Z) with respect to the second plate 1301, the biosensor 1360 may disposed below one area of the light guide structure 1340, and the illumination unit 1350 may be disposed below the other area of the light guide structure 1340.

According to various embodiments, the electronic device 1300 may include the biosensor 1360 for sensing biometric information of the user through an area of the second plate 1301. The biosensor may include a fingerprint sensor and/or an HRM sensor.

According to various embodiments, the illumination unit 1350, which provides light, may be disposed between a PCB 1370 and the light guide structure 1340, and may be electrically connected to the PCB 1370 so as to emit light. The PCB 1370 may be an FPCB. The illumination unit 1350 may be, for example, an IR LED module, and may radiate light to one face of the light guide structure 1340.

According to various embodiments, the light guide structure 1340 may be integrally fabricated using an acrylic material. The light guide structure 1340 may be designed to minimize the gap with the second plate 1301, and, for example, the gap between the second plate 1301 and the light guide structure 1340 may be implemented to be 0.1 T or less. Accordingly, it is possible to reduce the loss of light emitted from the illumination unit 1350 or received by the biosensor 1360, thereby improving the performance of the sensor. Detailed descriptions of FIGS. 10 to 12 are applicable to the corresponding configurations.

According to an embodiment of the disclosure, an electronic device may include: a housing including a first glass plate, a second glass plate facing away from the first glass plate, and a side member surrounding a space between the first glass plate and the second glass plate, the second plate including an outer face facing away from the first plate and an inner face facing the first plate; an inner intermediate plate located between the first plate and the second plate; a touch screen display located between the intermediate plate and the first plate; an opaque layer including a first opening and a second opening located within a distance of 150 mm from the first opening, the opaque layer directly or indirectly attached to the inner face of the second plate that includes a hole overlapping the first opening but does not include a hole overlapping the second opening; a camera assembly having a portion positioned in the hole of the second plate and the first opening; a Light-Emitting Diode (LED) positioned between first portions of the second opening while facing the second opening, and functionally connected to the camera assembly; a Heart Rate Monitor (HRM) assembly positioned between second portions of the second opening while facing the second opening, the second opening having a gap between the HRM assembly and an inner face of the second plate, and the HRB assembly including a light-emitting element and a light-receiving element; and a light guide structure including a first portion between the LED and the second plate and a second portion between the HRM assembly and the second plate, the first portion surrounding the LED and the second portion surrounding the light-emitting element when viewed from above the second plate. The HRM assembly may include a light-emitting element and a light-receiving element.

According to an embodiment of the disclosure, the electronic device may further include an optically clear adhesive layer located between the inner face of the second plate and the light guide structure.

According to an embodiment of the disclosure, the electronic device may further include an annular strip located between the inner face of the second plate and the biosensor assembly, the annular strip surrounding at least one portion of the biosensor assembly when viewed from above the second plate, and the annular strip may have a color different from a color of the opaque layer.

According to an embodiment of the disclosure, the light-receiving element may be located between the light-emitting element and the LED when viewed from above the second plate.

According to an embodiment of the disclosure, the light guide structure may include at least one shielding wall disposed between the light-emitting element and the light-receiving element to partition the light-emitting element and the light-receiving element.

According to an embodiment of the disclosure, the electronic device may further include a bracket disposed between the second plate of the housing and the light guide structure, and having at least one opening in an area corresponding to at least a portion of the first portion or the second portion of the light guide structure.

According to an embodiment of the disclosure, a portion formed to protrude on the first portion of the light guide structure may be disposed to be inserted into the at least one opening in the bracket.

According to an embodiment of the disclosure, the opaque layer may include a third opening disposed adjacent to the first opening, and the second plate includes a hole overlapping the third opening, and the electronic device may further include a fingerprint sensor partially located in the hole and the third opening when viewed from above the second plate.

According to an embodiment of the disclosure, the fingerprint sensor may be disposed to correspond to the HRM assembly with reference to the camera assembly, and the fingerprint sensor and the camera assembly may be partially exposed through the at least one opening of the second plate.

According to an embodiment of the disclosure, an electronic device may include: a housing including a display device including a first glass plate exposed to be oriented in a first direction and a second glass plate face oriented in a second direction to face away from the first glass plate, the housing further including a transparent area that forms at least a portion of the second plate; a printed circuit unit disposed inside the housing; an illumination unit disposed between the transparent area and the printed circuit board and electrically connected to the printed circuit board, the illumination unit being configured to emit light towards the transparent area; and a biosensor disposed between the transparent area and the printed circuit board and electrically connected to at least a portion of the printed circuit board so as to sense light transmitted through the transparent area.

According to an embodiment of the disclosure, the electronic device may further include a light guide structure disposed to face the transparent area of the second plate and configured to guide a path of the light emitted from the illumination unit and a path of the light provided to the biosensor, According to an embodiment of the disclosure, the biosensor may include a fingerprint sensor, and the second plate may include glass and an opening corresponding to the transparent area.

According to an embodiment of the disclosure, the light guide structure may include: a first portion including a transparent material formed to protrude in the second direction, and configured to guide a path of the light, which is emitted from the illumination unit, into the light guide structure; and a second portion including an open area corresponding to the biosensor, and configured to guide a path of the light, which is emitted from the illumination unit and at least a part of which is reflected from a portion of an external object, into the opening to be directed to the fingerprint sensor.

According to an embodiment of the disclosure, the light guide structure may include at least one shielding wall disposed between the first portion and the second portion so as to partition the illumination unit and the biosensor.

According to an embodiment of the disclosure, the electronic device may further include a bracket disposed between the second plate of the housing and the light guide structure, and having at least one opening in an area corresponding to at least a portion of the first portion or the second portion of the light guide structure.

According to an embodiment of the disclosure, the bracket may include a camera area in which at least a portion of at least one camera assembly exposed to the hole in the second plate, and a biometric sensing area in which the biosensor and the illumination unit are disposed, the biometric sensing area being disposed adjacent to the camera area.

According to an embodiment of the disclosure, the biosensor may be disposed on a plane which is a same as the illumination unit, and may include any one of a fingerprint sensor and an HRM sensor.

According to an embodiment of the disclosure, the illumination unit may be switchable to provide illumination to an outside or to provide a light source of the biosensor.

According to an embodiment of the disclosure, the biosensor disposed in the transparent area of the second plate includes a fingerprint sensor an HRM sensor disposed on the same plane as the fingerprint sensor, and at least one illumination unit may be disposed on a side of the fingerprint sensor or the HRM.

According to an embodiment of the disclosure, the light guide structure may include a guide structure having a plate shape including a transparent material and an acrylic material.

While the disclosure has been shown and described with reference to certain embodiments thereof, it will be apparent to those skilled in the art that the camera lens module according to the disclosure is not limited to these embodiments, and various changes in form and details may be made therein without departing from the spirit and scope of the disclosure as defined by the appended claims.

What is claimed is:

1. An electronic device comprising:
a housing including a first plate, a second plate formed of a transparent glass facing away from the first plate, and a side member surrounding a space between the first plate and the second plate, the second plate including an outer face facing away from the first plate and an inner face facing the first plate, and wherein the second plate includes a first hole;
an inner intermediate plate located between the first plate and the second plate;
a touch screen display located between the intermediate plate and the first plate;
an opaque layer attached directly to the inner face of the second plate, wherein the opaque layer is configured to visually hide an inside of the housing from an outside of the housing, wherein the opaque layer includes a first opening disposed to correspond to the first hole and a second opening disposed adjacent to the first opening, and wherein the second opening is configured to provide a transparent area in at least a portion of the second plate corresponding to the second opening such that the transparent area seamlessly is connected to the outer face of the second plate and provide a light path from the inside of the housing to the outside of the housing through the second plate, and the second opening positioned within 150 mm from the first opening and the first hole is overlapped with the first opening, not with the second opening;
a camera assembly positioned partly in the first hole of the second plate and the first opening;
a light emitting diode (LED) positioned between a first portions of the second opening while facing toward the second opening, wherein the LED is operatively connected to the camera assembly;
a heart rate monitor (HRM) assembly positioned between a second portions of the second opening while facing toward the second opening with a gap between the HRM assembly and the inner face of the second plate, wherein the HRM assembly includes a light emitting element and a light receiving element; and
a light guide structure including a first portion between the LED and the second plate and a second portion between the HRM assembly and the second plate, the first portion surrounding the LED and the second portion surrounding the light emitting element when viewed from above the second plate.

2. The electronic device of claim 1, further comprising:
an optically clear adhesive layer located between the inner face of the second plate and the light guide structure.

3. The electronic device of claim 2, further comprising:
an annular strip located between the inner face of the second plate and a biosensor assembly, the annular strip surrounding at least one portion of the biosensor assembly when viewed from above the second plate,
wherein the annular strip has a color different from a color of the opaque layer.

4. The electronic device of claim 3, wherein the light receiving element located between the light emitting element and the LED when viewed from above the second plate.

5. The electronic device of claim 3, wherein the light guide structure includes at least one shielding wall disposed between the light emitting element and the light receiving element to partition the light emitting element and the light receiving element.

6. The electronic device of claim 3, further comprising:
a bracket disposed between the second plate of the housing and the light guide structure, and having at least one opening in an area corresponding to at least a portion of the first portion or the second portion of the light guide structure.

7. The electronic device of claim 6, wherein a protruding portion formed on the first portion of the light guide structure is disposed to be inserted into the at least one opening in the bracket.

8. The electronic device of claim 7, wherein the opaque layer includes a third opening disposed adjacent to the first opening, and the second plate includes a second hole overlapping the third opening, and
the electronic device further comprises a fingerprint sensor partially located in the second hole and the third opening when viewed from above the second plate.

9. The electronic device of claim 8, wherein the fingerprint sensor is disposed to correspond to the HRM assembly with reference to the camera assembly, and
the fingerprint sensor and the camera assembly are partially exposed through the at least one opening of the second plate.

10. An electronic device comprising:
a housing including a display device including a first glass plate exposed to be oriented in a first direction and a second glass plate face oriented in a second direction to face away from the first glass plate;
an opaque layer attached directly to an inner face of the second glass plate, wherein the opaque layer is configured to visually hide an inside of the housing from an outside of the housing, wherein the opaque layer includes a first opening disposed to correspond to a first hole and a second opening disposed adjacent to the first opening, and wherein the second opening is configured to provide a transparent area in at least a portion of the second glass plate corresponding to the second opening such that the transparent area seamlessly is connected to an outer face of the second glass plate and provide a light path from the inside of the housing to the outside of the housing through the second glass plate, and the second opening positioned within 150 mm from the first opening and the first hole is overlapped with the first opening, not with the second opening;
a printed circuit board disposed inside the housing;
an illumination unit disposed between the transparent area and the printed circuit board and electrically connected to the printed circuit board, the illumination unit being configured to emit light towards the transparent area; and
a biosensor disposed between the transparent area and the printed circuit board and electrically connected to at least a portion of the printed circuit board so as to sense light transmitted through the transparent area.

11. The electronic device of claim 10, further comprising:
a light guide structure disposed to face the transparent area of the second glass plate and configured to guide a path of the light emitted from the illumination unit and a path of the light provided to the biosensor,
wherein the biosensor includes a fingerprint sensor, and the second glass plate includes glass and an opening corresponding to the transparent area.

12. The electronic device of claim 11, wherein the light guide structure includes:
a first portion including a transparent material formed to protrude in the second direction, and configured to guide a path of the light, which is emitted from the illumination unit, into the light guide structure,
a second portion including an open area corresponding to the biosensor, and configured to guide a path of the light, which is emitted from the illumination unit and at least a part of which is reflected from a portion of an external object, into the opening to be directed to the fingerprint sensor, and
at least one shielding wall disposed between the first portion and the second portion so as to partition the illumination unit and the biosensor.

13. The electronic device of claim 12, further comprising:
a bracket disposed between the second glass plate of the housing and the light guide structure, and having at least one opening in an area corresponding at least a portion of the first portion or the second portion of the light guide structure,
wherein the bracket includes a camera area in which at least a portion of at least one camera assembly exposed to a hole in the second glass plate, and a biometric sensing area in which the biosensor and the illumination unit are disposed, the biometric sensing area being disposed adjacent to the camera area.

14. The electronic device of claim 11, wherein the biosensor is disposed on a plane which is a same as the illumination unit, and includes any one of a fingerprint sensor and an HRM sensor, and
the illumination unit is switchable to provide illumination to an outside or to provide a light source of the biosensor.

15. The electronic device of claim 12, wherein the light guide structure includes a guide structure having a plate shape and including a transparent material and includes an acrylic material.

* * * * *